United States Patent
Li et al.

(10) Patent No.: US 10,052,415 B2
(45) Date of Patent: *Aug. 21, 2018

(54) TROPOELASTIN FOR PROMOTING ENDOTHELIAL CELL ADHESION OR MIGRATION

(71) Applicant: University of Utah Research Foundation, Salt Lake City, UT (US)

(72) Inventors: Dean Y. Li, Salt Lake City, UT (US); Brent D. Wilson, Salt Lake City, UT (US); Lise Sorensen Brunhart, Salt Lake City, UT (US)

(73) Assignee: University of Utah Research Foundation, Salt Lake City, UT (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/173,376

(22) Filed: Jun. 3, 2016

(65) Prior Publication Data

US 2016/0346440 A1 Dec. 1, 2016

Related U.S. Application Data

(63) Continuation of application No. 14/446,973, filed on Jul. 30, 2014, now Pat. No. 9,381,282, which is a continuation of application No. 11/885,105, filed as application No. PCT/US2006/006526 on Feb. 24, 2006, now Pat. No. 9,005,356.

(60) Provisional application No. 60/656,360, filed on Feb. 25, 2005.

(51) Int. Cl.
| | |
|---|---|
| *A61K 38/39* | (2006.01) |
| *A61L 27/28* | (2006.01) |
| *A61L 31/16* | (2006.01) |
| *A61L 27/22* | (2006.01) |
| *A61K 9/28* | (2006.01) |
| *A61L 27/34* | (2006.01) |
| *A61L 27/38* | (2006.01) |
| *A61L 27/54* | (2006.01) |
| *A61L 29/04* | (2006.01) |
| *A61L 29/08* | (2006.01) |
| *A61L 29/16* | (2006.01) |
| *A61L 31/04* | (2006.01) |
| *A61L 31/10* | (2006.01) |
| *A61N 1/362* | (2006.01) |
| *A61N 1/39* | (2006.01) |

(52) U.S. Cl.
CPC .............. *A61L 31/16* (2013.01); *A61K 38/39* (2013.01); *A61L 27/227* (2013.01); *A61L 27/34* (2013.01); *A61L 27/3808* (2013.01); *A61L 27/3895* (2013.01); *A61L 27/54* (2013.01); *A61L 29/048* (2013.01); *A61L 29/085* (2013.01); *A61L 29/16* (2013.01); *A61L 31/047* (2013.01); *A61L 31/10* (2013.01); *A61N 1/362* (2013.01); *A61N 1/3956* (2013.01); *A61L 2300/416* (2013.01); *A61L 2300/42* (2013.01); *A61L 2300/61* (2013.01); *A61L 2400/18* (2013.01)

(58) Field of Classification Search
None
See application file for complete search history.

(56) References Cited

U.S. PATENT DOCUMENTS 7,001,328 B1 * 2/2006 Barofsky .............. A61L 27/227
 600/36
7,125,837 B1 * 10/2006 Keating ................. A61K 38/39
 424/185.1

* cited by examiner

*Primary Examiner* — Manjunath N Rao
*Assistant Examiner* — Samuel W Liu
(74) *Attorney, Agent, or Firm* — Leason Ellis LLP

(57) ABSTRACT

The invention provides methods, compositions, and devices for promoting adhesion or migration of endothelial cell.

14 Claims, 7 Drawing Sheets

SEQUENCE LISTING

<160> NUMBER OF SEQ ID NOS: 7

<210> SEQ ID NO 1
<211> LENGTH: 2274
<212> TYPE: DNA
<213> ORGANISM: Homo sapiens

<400> SEQUENCE: 1

| | | | | | | |
|---|---|---|---|---|---|---|
| atggcgggtc | tgacggcggc | ggccccgcgg | cccggagtcc | tcctgctcct | gctgtccatc | 60 |
| ctccacccct | ctcggcctgg | aggggtccct | ggggccattc | ctggtggagt | tcctggagga | 120 |
| gtcttttatc | caggggctgg | tctcggagcc | cttggaggag | gagcgctggg | gcctggaggc | 180 |
| aaacctctta | agccagttcc | cggagggctt | gcggtgctg | gccttggggc | agggctcggc | 240 |
| gccttccccg | cagttacctt | tccgggggct | ctggtgcctg | gtggagtggc | tgacgctgct | 300 |
| gcagcctata | aagctgctaa | ggctggcgct | gggcttggtg | gtgtcccagg | agttggtggc | 360 |
| ttaggagtgt | ctgcaggtgc | ggtggttcct | cagcctggac | ccggagtgaa | gcctgggaaa | 420 |
| gtgccgggtg | tggggctgcc | aggtgtatac | ccaggtggcg | tgctcccagg | agctcggttc | 480 |
| cccggtgtgg | ggtgctccc | tggagttccc | actggagcag | gagttaagcc | caaggctcca | 540 |
| ggtgtaggtg | gagcttttgc | tggaatccca | ggagttggac | cctttggggg | accgcaacct | 600 |
| ggagtcccac | tggggtatcc | catcaaggcc | cccaagctgc | ctggtggcta | tggactgccc | 660 |
| tacaccacag | ggaaactgcc | ctatggctat | gggcccggag | gagtggctgg | tgcagcgggc | 720 |
| aaggctggtt | acccaacagg | gacaggggtt | ggccccagg | cagcagcagc | agcggcagct | 780 |
| aaagcagcag | caaagttcgg | tgctggagca | gccggagtcc | tccctggtgt | tggaggggct | 840 |
| ggtgttcctg | gcgtgcctgg | ggcaattcct | ggaattggag | gcatcgcagg | cgttgggact | 900 |
| ccagctgcag | ctgcagctgc | agcagcagcc | gctaaggcag | ccaagtatgg | agctgctgca | 960 |
| ggcttagtgc | ctggtgggcc | aggctttggc | ccggagtag | ttggtgtccc | aggagctggc | 1020 |
| gttccaggtg | ttggtgtccc | aggagctggg | attccagttg | tccaggtgc | tgggatccca | 1080 |
| ggtgctgcgg | ttccagggt | tgtgtcacca | gaagcagctg | ctaaggcagc | tgcaaaggca | 1140 |
| gccaaatacg | gggccaggcc | cggagtcgga | gttggaggca | ttcctactta | cggggttgga | 1200 |
| gctgggggct | ttccccggctt | tggtgtcgga | gtcggaggta | tccctggagt | cgcaggtgtc | 1260 |
| cctagtgtcg | gaggtgttcc | cggagtcgga | ggtgtcccgg | gagttggcat | tcccccgaa | 1320 |
| gctcaggcag | cagctgccgc | caaggctgcc | aagtacggag | tggggacccc | agcagctgca | 1380 |
| gctgctaaag | cagccgccaa | agccgcccag | tttgggttag | ttcctggtgt | cggcgtggct | 1440 |
| cctggagttg | gcgtggctcc | tggtgtcggt | gtggctcctg | gagttggctt | ggctcctgga | 1500 |
| gttggcgtgg | ctcctggagt | tggtgtggct | cctggcgttg | gcgtggctcc | cggcattggc | 1560 |
| cctggtggag | ttgcagctgc | agcaaaaatcc | gctgccaagg | tggctgccaa | agcccagctc | 1620 |
| cgagctgcag | ctgggcttgg | tgctggcatc | cctggacttg | gagttggtgt | cggcgtccct | 1680 |
| ggacttggag | ttggtgctgg | tgttcctgga | cttggagttg | gtgctggtgt | tcctggcttc | 1740 |
| ggggcaggtg | cagatgaggg | agttaggcgg | agcctgtccc | ctgagctcag | ggaaggagat | 1800 |
| ccctcctcct | ctcagcacct | ccccagcacc | ccctcatcac | ccagggtacc | tggagccctg | 1860 |
| gctgccgcta | aagcagccaa | atatggagca | gcagtgcctg | gggtccttgg | agggctcggg | 1920 |
| gctctcggtg | gagtaggcat | cccaggcggt | gtggtgggag | ccggaccgc | gccgccgct | 1980 |
| gccgcagcca | aagctgctgc | caaagccgcc | cagtttggcc | tagtgggagc | cgctgggctc | 2040 |
| ggaggactcg | gagtcggagg | gcttggagtt | ccaggtgttg | ggggccttgg | aggtatacct | 2100 |

```
ccagctgcag ccgctaaagc agctaaatac ggtgctgctg gccttggagg tgtcctaggg    2160
ggtgccgggc agttcccact tggaggagtg cagcaagac ctggcttcgg attgtctccc    2220
attttcccag gtggggcctg cctggggaaa gcttgtggcc ggaagagaaa atga         2274
```

<210> SEQ ID NO 2
<211> LENGTH: 757
<212> TYPE: PRT
<213> ORGANISM: Homo sapiens

<400> SEQUENCE: 2

```
Met Ala Gly Leu Thr Ala Ala Pro Arg Pro Gly Val Leu Leu Leu
 1               5                  10                  15

Leu Leu Ser Ile Leu His Pro Ser Arg Pro Gly Gly Val Pro Gly Ala
                20                  25                  30

Ile Pro Gly Gly Val Pro Gly Gly Val Phe Tyr Pro Gly Ala Gly Leu
                35                  40                  45

Gly Ala Leu Gly Gly Gly Ala Leu Gly Pro Gly Gly Lys Pro Leu Lys
                50                  55                  60

Pro Val Pro Gly Gly Leu Ala Gly Ala Gly Leu Gly Ala Gly Leu Gly
 65                  70                  75                  80

Ala Phe Pro Ala Val Thr Phe Pro Gly Ala Leu Val Pro Gly Gly Val
                    85                  90                  95

Ala Asp Ala Ala Ala Ala Tyr Lys Ala Ala Lys Ala Gly Ala Gly Leu
                100                 105                 110

Gly Gly Val Pro Gly Val Gly Gly Leu Gly Val Ser Ala Gly Ala Val
                115                 120                 125

Val Pro Gln Pro Gly Ala Gly Val Lys Pro Gly Lys Val Pro Gly Val
                130                 135                 140

Gly Leu Pro Gly Val Tyr Pro Gly Gly Val Leu Pro Gly Ala Arg Phe
145                 150                 155                 160

Pro Gly Val Gly Val Leu Pro Gly Val Pro Thr Gly Ala Gly Val Lys
                165                 170                 175

Pro Lys Ala Pro Gly Val Gly Gly Ala Phe Ala Gly Ile Pro Gly Val
                180                 185                 190

Gly Pro Phe Gly Gly Pro Gln Pro Gly Val Pro Leu Gly Tyr Pro Ile
                195                 200                 205

Lys Ala Pro Lys Leu Pro Gly Gly Tyr Gly Leu Pro Tyr Thr Thr Gly
                210                 215                 220

Lys Leu Pro Tyr Gly Tyr Gly Pro Gly Gly Val Ala Gly Ala Ala Gly
225                 230                 235                 240

Lys Ala Gly Tyr Pro Thr Gly Thr Gly Val Gly Pro Gln Ala Ala Ala
                245                 250                 255

Ala Ala Ala Ala Lys Ala Ala Lys Phe Gly Ala Gly Ala Ala Gly
                260                 265                 270

Val Leu Pro Gly Val Gly Gly Ala Gly Val Pro Gly Val Pro Gly Ala
                275                 280                 285

Ile Pro Gly Ile Gly Gly Ile Ala Gly Val Gly Thr Pro Ala Ala Ala
                290                 295                 300

Ala Ala Ala Ala Ala Ala Lys Ala Ala Lys Tyr Gly Ala Ala Ala
305                 310                 315                 320

Gly Leu Val Pro Gly Gly Pro Gly Phe Gly Pro Gly Val Val Gly Val
                325                 330                 335

Pro Gly Ala Gly Val Pro Gly Val Gly Val Pro Gly Ala Gly Ile Pro
```

```
                340             345             350
        Val Val Pro Gly Ala Ile Pro Gly Ala Val Pro Gly Val Val
                355             360             365
        Ser Pro Glu Ala Ala Ala Lys Ala Ala Lys Ala Ala Lys Tyr Gly
                370             375             380
        Ala Arg Pro Gly Val Gly Val Gly Gly Ile Pro Thr Tyr Gly Val Gly
        385             390             395             400
        Ala Gly Gly Phe Pro Gly Phe Gly Val Gly Val Gly Gly Ile Pro Gly
                            405             410             415
        Val Ala Gly Val Pro Ser Val Gly Gly Val Pro Gly Val Gly Gly Val
                        420             425             430
        Pro Gly Val Gly Ile Ser Pro Glu Ala Gln Ala Ala Ala Ala Ala Lys
                    435             440             445
        Ala Ala Lys Tyr Gly Val Gly Thr Pro Ala Ala Ala Ala Ala Lys Ala
                    450             455             460
        Ala Ala Lys Ala Ala Gln Phe Gly Leu Val Pro Gly Val Gly Val Ala
        465             470             475             480
        Pro Gly Val Gly Val Ala Pro Gly Val Gly Val Ala Pro Gly Val Gly
                        485             490             495
        Leu Ala Pro Gly Val Gly Val Ala Pro Gly Val Gly Val Ala Pro Gly
                    500             505             510
        Val Gly Val Ala Pro Gly Ile Gly Pro Gly Gly Val Ala Ala Ala Ala
                    515             520             525
        Lys Ser Ala Ala Lys Val Ala Ala Lys Ala Gln Leu Arg Ala Ala Ala
                530             535             540
        Gly Leu Gly Ala Gly Ile Pro Gly Leu Gly Val Gly Val Gly Val Pro
        545             550             555             560
        Gly Leu Gly Val Gly Ala Gly Val Pro Gly Leu Gly Val Gly Ala Gly
                        565             570             575
        Val Pro Gly Phe Gly Ala Gly Ala Asp Glu Gly Val Arg Arg Ser Leu
                    580             585             590
        Ser Pro Glu Leu Arg Glu Gly Asp Pro Ser Ser Gln His Leu Pro
                    595             600             605
        Ser Thr Pro Ser Ser Pro Arg Val Pro Gly Ala Leu Ala Ala Ala Lys
                    610             615             620
        Ala Ala Lys Tyr Gly Ala Ala Val Pro Gly Val Leu Gly Gly Leu Gly
        625             630             635             640
        Ala Leu Gly Gly Val Gly Ile Pro Gly Gly Val Val Gly Ala Gly Pro
                        645             650             655
        Ala Ala Ala Ala Ala Ala Ala Lys Ala Ala Lys Ala Ala Gln Phe
                    660             665             670
        Gly Leu Val Gly Ala Ala Gly Leu Gly Gly Leu Gly Val Gly Gly Leu
                675             680             685
        Gly Val Pro Gly Val Gly Gly Leu Gly Gly Ile Pro Pro Ala Ala Ala
                690             695             700
        Ala Lys Ala Ala Lys Tyr Gly Ala Ala Gly Leu Gly Gly Val Leu Gly
        705             710             715             720
        Gly Ala Gly Gln Phe Pro Leu Gly Gly Val Ala Ala Arg Pro Gly Phe
                        725             730             735
        Gly Leu Ser Pro Ile Phe Pro Gly Gly Ala Cys Leu Gly Lys Ala Cys
                    740             745             750
        Gly Arg Lys Arg Lys
                    755
```

<210> SEQ ID NO 3
<211> LENGTH: 712
<212> TYPE: PRT
<213> ORGANISM: Homo sapiens

<400> SEQUENCE: 3

```
Met Ala Gly Leu Thr Ala Ala Pro Arg Pro Gly Val Leu Leu Leu
 1               5                  10                  15

Leu Leu Ser Ile Leu His Pro Ser Arg Pro Gly Gly Val Pro Gly Ala
             20                  25                  30

Ile Pro Gly Gly Val Pro Gly Gly Val Phe Tyr Pro Gly Ala Gly Leu
             35                  40                  45

Gly Ala Leu Gly Gly Gly Ala Leu Gly Pro Gly Gly Lys Pro Leu Lys
         50                  55                  60

Pro Val Pro Gly Gly Leu Ala Gly Ala Gly Leu Gly Ala Gly Leu Gly
 65                  70                  75                  80

Ala Phe Pro Ala Val Thr Phe Pro Gly Ala Leu Val Pro Gly Gly Val
                 85                  90                  95

Ala Asp Ala Ala Ala Ala Tyr Lys Ala Ala Lys Ala Gly Ala Gly Leu
                100                 105                 110

Gly Gly Val Pro Gly Val Gly Gly Leu Gly Val Ser Ala Gly Ala Val
            115                 120                 125

Val Pro Gln Pro Gly Ala Gly Val Lys Pro Gly Lys Val Pro Gly Val
            130                 135                 140

Gly Leu Pro Gly Val Tyr Pro Gly Gly Val Leu Pro Gly Ala Arg Phe
145                 150                 155                 160

Pro Gly Val Gly Val Leu Pro Gly Val Pro Thr Gly Ala Gly Val Lys
                165                 170                 175

Pro Lys Ala Pro Gly Val Gly Gly Ala Phe Ala Gly Ile Pro Gly Val
            180                 185                 190

Gly Pro Phe Gly Gly Pro Gln Pro Gly Val Pro Leu Gly Tyr Pro Ile
            195                 200                 205

Lys Ala Pro Lys Leu Pro Gly Gly Tyr Gly Leu Pro Tyr Thr Thr Gly
        210                 215                 220

Lys Leu Pro Tyr Gly Tyr Gly Pro Gly Gly Val Ala Gly Ala Ala Gly
225                 230                 235                 240

Lys Ala Gly Tyr Pro Thr Gly Thr Gly Val Gly Pro Gln Ala Ala Ala
                245                 250                 255

Ala Ala Ala Ala Lys Ala Ala Lys Phe Gly Ala Gly Ala Ala Gly
            260                 265                 270

Val Leu Pro Gly Val Gly Gly Ala Gly Val Pro Gly Val Pro Gly Ala
            275                 280                 285

Ile Pro Gly Ile Gly Gly Ile Ala Gly Val Gly Thr Pro Ala Ala Ala
            290                 295                 300

Ala Ala Ala Ala Ala Ala Lys Ala Ala Lys Tyr Gly Ala Ala Ala
305                 310                 315                 320

Gly Leu Val Pro Gly Gly Pro Gly Phe Gly Pro Gly Val Val Gly Val
                325                 330                 335

Pro Gly Ala Gly Val Pro Gly Val Gly Val Pro Gly Ala Gly Ile Pro
            340                 345                 350

Val Val Pro Gly Ala Gly Ile Pro Gly Ala Ala Val Pro Gly Val Val
            355                 360                 365

Ser Pro Glu Ala Ala Ala Lys Ala Ala Ala Lys Ala Ala Lys Tyr Gly
```

```
                370                 375                 380
Ala Arg Pro Gly Val Gly Val Gly Ile Pro Thr Tyr Gly Val Gly
385                 390                 395                 400

Ala Gly Gly Phe Pro Gly Phe Gly Val Gly Val Gly Ile Pro Gly
                405                 410                 415

Val Ala Gly Val Pro Gly Val Gly Val Pro Gly Val Gly Gly Val
                420                 425                 430

Pro Gly Val Gly Ile Ser Pro Glu Ala Gln Ala Ala Ala Ala Lys
                435                 440                 445

Ala Ala Lys Tyr Gly Val Gly Thr Pro Ala Ala Ala Ala Lys Ala
                450                 455                 460

Ala Ala Lys Ala Ala Gln Phe Ala Leu Leu Asn Leu Ala Gly Leu Val
465                 470                 475                 480

Pro Gly Val Gly Val Ala Pro Gly Val Gly Val Ala Pro Gly Val Gly
                485                 490                 495

Val Ala Pro Gly Val Gly Leu Ala Pro Gly Val Gly Val Ala Pro Gly
                500                 505                 510

Val Gly Val Ala Pro Gly Val Gly Val Ala Pro Gly Ile Gly Pro Gly
                515                 520                 525

Gly Val Ala Ala Ala Lys Ser Ala Ala Lys Val Ala Ala Lys Ala
                530                 535                 540

Gln Leu Arg Ala Ala Ala Gly Leu Gly Ala Gly Ile Pro Gly Leu Gly
545                 550                 555                 560

Val Gly Val Gly Val Pro Gly Leu Gly Val Gly Ala Gly Val Pro Gly
                565                 570                 575

Leu Gly Val Gly Ala Gly Val Pro Gly Phe Gly Ala Val Pro Gly Ala
                580                 585                 590

Leu Ala Ala Ala Lys Ala Ala Lys Tyr Gly Ala Ala Val Pro Gly Val
                595                 600                 605

Leu Gly Gly Leu Gly Ala Leu Gly Gly Val Gly Ile Pro Gly Gly Val
                610                 615                 620

Val Gly Ala Gly Pro Ala Ala Ala Ala Ala Ala Lys Ala Ala Ala
625                 630                 635                 640

Lys Ala Ala Gln Phe Gly Leu Val Gly Ala Ala Gly Leu Gly Gly Leu
                645                 650                 655

Gly Val Gly Gly Leu Gly Val Pro Gly Val Gly Gly Leu Gly Gly Ile
                660                 665                 670

Pro Pro Ala Ala Ala Ala Lys Ala Ala Lys Tyr Gly Val Ala Ala Arg
                675                 680                 685

Pro Gly Phe Gly Leu Ser Pro Ile Phe Pro Gly Gly Ala Cys Leu Gly
                690                 695                 700

Lys Ala Cys Gly Arg Lys Arg Lys
705                 710

<210> SEQ ID NO 4
<211> LENGTH: 706
<212> TYPE: PRT
<213> ORGANISM: Homo sapiens

<400> SEQUENCE: 4

Met Gly His His His His His His His His Ser Ser Gly Gly
1                   5                  10                  15

Ile Glu Gly Arg Gly Gly Val Pro Gly Ala Ile Pro Gly Gly Val Pro
                20                  25                  30
```

-continued

```
Gly Gly Val Phe Tyr Pro Gly Ala Gly Leu Gly Gly Gly
         35              40              45
Ala Leu Gly Pro Gly Gly Lys Pro Leu Lys Pro Val Pro Gly Gly Leu
50                  55                  60
Ala Gly Ala Gly Leu Gly Ala Gly Leu Gly Ala Phe Pro Ala Val Thr
65                  70                  75                  80
Phe Pro Gly Ala Leu Val Pro Gly Gly Val Ala Asp Ala Ala Ala
                 85                  90                  95
Tyr Lys Ala Ala Lys Ala Gly Ala Gly Leu Gly Gly Val Pro Gly Val
             100                 105                 110
Gly Gly Leu Gly Val Ser Ala Gly Ala Val Val Pro Gln Pro Gly Ala
             115                 120                 125
Gly Val Lys Pro Gly Lys Val Pro Gly Val Gly Leu Pro Gly Val Tyr
         130                 135                 140
Pro Gly Gly Val Leu Pro Gly Ala Arg Phe Pro Gly Val Gly Val Leu
145                 150                 155                 160
Pro Gly Val Pro Thr Gly Ala Gly Val Lys Pro Lys Ala Pro Gly Val
                 165                 170                 175
Gly Gly Ala Phe Ala Gly Ile Pro Gly Val Gly Pro Phe Gly Gly Pro
             180                 185                 190
Gln Pro Gly Val Pro Leu Gly Tyr Pro Ile Lys Ala Pro Lys Leu Pro
             195                 200                 205
Gly Gly Tyr Gly Leu Pro Tyr Thr Thr Gly Lys Leu Pro Tyr Gly Tyr
         210                 215                 220
Gly Pro Gly Gly Val Ala Gly Ala Ala Gly Lys Ala Gly Tyr Pro Thr
225                 230                 235                 240
Gly Thr Gly Val Gly Pro Gln Ala Ala Ala Ala Ala Ala Lys Ala
                 245                 250                 255
Ala Ala Lys Phe Gly Ala Gly Ala Ala Gly Val Leu Pro Gly Val Gly
             260                 265                 270
Gly Ala Gly Val Pro Gly Val Pro Gly Ala Ile Pro Gly Ile Gly Gly
         275                 280                 285
Ile Ala Gly Val Gly Thr Pro Ala Ala Ala Ala Ala Ala Ala Ala
290                 295                 300
Ala Lys Ala Ala Lys Tyr Gly Ala Ala Ala Gly Leu Val Pro Gly Gly
305                 310                 315                 320
Pro Gly Phe Gly Pro Gly Val Val Gly Val Pro Gly Ala Gly Val Pro
                 325                 330                 335
Gly Val Gly Val Pro Gly Ala Gly Ile Pro Val Val Pro Gly Ala Gly
             340                 345                 350
Ile Pro Gly Ala Ala Val Pro Gly Val Val Ser Pro Glu Ala Ala Ala
             355                 360                 365
Lys Ala Ala Ala Lys Ala Ala Lys Tyr Gly Ala Arg Pro Gly Val Gly
         370                 375                 380
Val Gly Gly Ile Pro Thr Tyr Gly Val Gly Ala Gly Gly Phe Pro Gly
385                 390                 395                 400
Phe Gly Val Gly Val Gly Gly Ile Pro Gly Val Ala Gly Val Pro Gly
                 405                 410                 415
Val Gly Gly Val Pro Gly Val Gly Gly Val Pro Gly Val Gly Ile Ser
             420                 425                 430
Pro Glu Ala Gln Ala Ala Ala Ala Ala Lys Ala Ala Lys Tyr Gly Val
             435                 440                 445
Gly Thr Pro Ala Ala Ala Ala Ala Lys Ala Ala Ala Lys Ala Ala Gln
```

```
                450                 455                 460
Phe Ala Leu Leu Asn Leu Ala Gly Leu Val Pro Gly Val Gly Val Ala
465                 470                 475                 480

Pro Gly Val Gly Val Ala Pro Gly Val Gly Val Ala Pro Gly Val Gly
                485                 490                 495

Leu Ala Pro Gly Val Gly Val Ala Pro Gly Val Gly Val Ala Pro Gly
                500                 505                 510

Val Gly Val Ala Pro Gly Ile Gly Pro Gly Gly Val Ala Ala Ala
                515                 520                 525

Lys Ser Ala Ala Lys Val Ala Ala Lys Ala Gln Leu Arg Ala Ala Ala
    530                 535                 540

Gly Leu Gly Ala Gly Ile Pro Gly Leu Gly Val Gly Val Gly Val Pro
545                 550                 555                 560

Gly Leu Gly Val Gly Ala Gly Val Pro Gly Leu Gly Val Gly Ala Gly
                565                 570                 575

Val Pro Gly Phe Gly Ala Val Pro Gly Ala Leu Ala Ala Ala Lys Ala
                580                 585                 590

Ala Lys Tyr Gly Ala Ala Val Pro Gly Val Leu Gly Gly Leu Gly Ala
    595                 600                 605

Leu Gly Gly Val Gly Ile Pro Gly Gly Val Val Gly Ala Gly Pro Ala
    610                 615                 620

Ala Ala Ala Ala Ala Ala Lys Ala Ala Ala Lys Ala Ala Gln Phe Gly
625                 630                 635                 640

Leu Val Gly Ala Ala Gly Leu Gly Gly Leu Gly Val Gly Gly Leu Gly
                645                 650                 655

Val Pro Gly Val Gly Gly Leu Gly Gly Ile Pro Pro Ala Ala Ala Ala
                660                 665                 670

Lys Ala Ala Lys Tyr Gly Val Ala Ala Arg Pro Gly Phe Gly Leu Ser
    675                 680                 685

Pro Ile Phe Pro Gly Gly Ala Cys Leu Gly Lys Ala Cys Gly Arg Lys
    690                 695                 700

Arg Lys
705

<210> SEQ ID NO 5
<211> LENGTH: 6
<212> TYPE: PRT
<213> ORGANISM: Artificial Sequence
<220> FEATURE:
<223> OTHER INFORMATION: chemically synthesized bioactive fragment of
      tropoelastin

<400> SEQUENCE: 5

Val Gly Val Ala Pro Gly
1               5

<210> SEQ ID NO 6
<211> LENGTH: 17
<212> TYPE: PRT
<213> ORGANISM: Artificial Sequence
<220> FEATURE:
<223> OTHER INFORMATION: chemically synthesized  bioactive fragment of
      tropoelastin

<400> SEQUENCE: 6

Ile Phe Pro Gly Gly Ala Cys Leu Gly Lys Ala Cys Gly Arg Lys Arg
1               5                   10                  15

Lys
```

```
<210> SEQ ID NO 7
<211> LENGTH: 6
<212> TYPE: PRT
<213> ORGANISM: Artificial Sequence
<220> FEATURE:
<223> OTHER INFORMATION: chemically synthesized fragment

<400> SEQUENCE: 7

Gly Pro Ala Val Gly Val
 1               5
```

TROPOELASTIN FOR PROMOTING ENDOTHELIAL CELL ADHESION OR MIGRATION

RELATED APPLICATIONS

This application is a continuation of U.S. application Ser. No. 14/446,973, filed on Jul. 30, 2014, which is a continuation of U.S. application Ser. No. 11/885,105, filed on Jul. 15, 2009, which is a 371 National Stage of International Application No. PCT/US2006/006526, filed on Feb. 24, 2006, which claims priority to U.S. Provisional Application No. 60/656,360, filed on Feb. 25, 2005, the contents of all of which are hereby incorporated by reference in their entireties.

This invention was made with government support under R01 HL068873 awarded by the National Institutes of Health. The government has certain rights in the invention.

INCORPORATION-BY-REFERENCE OF SEQUENCE LISTING

A sequence listing, created on Jun. 3, 2016 as the ASCII text file "11202-004938-US3_SeqListing.txt" having a file size of 22 kilobytes, is incorporated herein by reference in its entirety.

BACKGROUND OF THE INVENTION

Advances in the treatment of cardiovascular diseases and obstructive vascular diseases have led to treatments for a range of illnesses and conditions. These treatments, which include implantation of numerous varieties of drug-eluting and non-drug-eluting devices, have dramatically improved survival and the quality of life of patients. However, these treatments are not without limitations and side-effects.

Medical therapies focus on reducing the risk factors associated with obstructive vascular disease. Anti-thrombotic, anti-hypertensive, and Cholesterol-lowering medications are aimed at decreasing the risk of occlusion, while beta-blockers and angiotensin-converting enzyme inhibitors act by reducing the workload of the heart. Despite these pharmaceutical advances that reduce the risk of vascular occlusion and cardiac events, the need for interventional cardiology and cardiac surgery to directly treat cardiovascular diseases and vascular obstructions remains immense.

Angioplasty is the major intervention for coronary artery disease accounting for over 680,000 procedures annually in the United States alone. Briefly, a balloon is placed within a blocked artery and expanded to relieve the obstruction. In most cases, a stent is placed within the instrumented artery. However, only 70% of angioplasties lead to long-term (6 months) relief of vascular obstruction. In a process termed restenosis, vascular smooth muscle cells reocclude the artery in response to the vascular injury caused by angioplasty. Such restenosis is also observed in other procedures which cause injury to a body vessel wall including the placement of stents, wires, catheters, shunts, or other intraluminal devices in any body vessel (e.g., in an artery, vein, ureter, urethra, Fallopian tube, common bile duct, pancreatic duct, kidney duct, esophagus, trachea, bladder, uterus, ovarian duct, vas deferens, prostatic duct, or lymphatic duct). Continued advances in the geometry and composition of stents have largely impacted ease of stent delivery, but have not lessened the complication of restenosis. Recently, strategies employing radioactivity and other cytotoxic agents (e.g. paclitaxil, actinomycinD, and rapamycin) to treat restenosis have received substantial attention. These strategies rely on the temporary and local delivery of toxic agents that block proliferation of many cell types. The long-term efficacy is currently being tested; however the toxicity of these agents raises serious doubts of whether they can be used as a long term treatment option for managing often chronic cardiac and cardiovascular conditions.

Current therapies for cardiovascular and obstructive vascular diseases aim to prevent or inhibit the hyperproliferation of the vascular smooth muscle cells lining vessels, thereby preventing or inhibiting occlusion of the vessel. However, many of the therapies, including rapamycin and taxol, used to inhibit proliferation of vascular smooth muscle cells function via a cytotoxic mechanism. Although these therapies may help prevent occlusion, their cytotoxicity inhibits endothelial coils within or adjacent to vessels. Damage to endothelial cell growth or structure is further exacerbated by insertion of intraluminal devices which are often used to deliver these and other therapeutic agents. A combination of the damage caused by the therapeutic agents and/or damage caused by the insertion of various devices often leads to restenosis. As a result of restenosis, patients with cardiovascular and occlusive vascular diseases must often be repeatedly stented, catheterized, or otherwise treated. Such repeated treatment exposes the patients to increased risks associated with any hospitalization or invasive procedure. Furthermore, the need to repeat these treatments dramatically increases the costs associated with managing these conditions. Methods and compositions that decrease or prevent restenosis would provide a substantial improvement in the art.

In addition to the problem of restenosis, thrombosis is a significant problem associated with many of the current treatments for cardiovascular diseases and occlusive vascular diseases. In fact, the risk of thrombosis exists whenever a device is placed and left in the body, and is thus a potential complication of many surgical procedures. Thus, thrombosis is a serious complication associated not only with cardiac and intravascular procedures, but also with other interventional approaches involving the placing of devices into the body or into the lumens of body vessels. Specifically, and as outlined above, many of the current drug therapies damage endothelial cells and then inhibit their proliferation. This significantly inhibits endothelialization of inserted devices. As a result, late thrombosis may occur in patients treated using a drug-eluting or non-drug-eluting device. To help prevent potentially lethal thrombosi, patients are often aggressively treated (sometimes on a long term basis) with anti-platelet and/or anti-coagulant therapies. These treatments impose their own risks and costs. Accordingly, methods and compositions that promote endothelization of inserted devices (e.g., intravascular or other intraluminal devices), thereby preventing or decreasing the likelihood of thrombosis would be a significant improvement in the art.

The present invention provides methods and compositions for promoting adhesion of endothelial cells, for example, for promoting adhesion of endothelial cells to implantable, biocompatible devices. Methods and compositions for promoting adhesion of endothelial cells, for example, to biocompatible devices, can be used in the treatment or prevention of restenosis and/or thrombosis.

SUMMARY OF THE INVENTION

The invention provides compositions and methods for modulating the adhesion and/or migration of endothelial cells. The invention provides compositions and methods for treating and preventing restenosis or thrombosis that often result as a potentially fatal side-effect of drug and device-based therapies for numerous cardiovascular diseases and obstructive vascular diseases. The invention further provides implantable devices designed to promote endothelial adhesion, thereby preventing restenosis or thrombosis.

In a first aspect, the invention provides a method of promoting adhesion of endothelial cells. The method comprises contacting said endothelial cells with an amount of a composition comprising an effective amount of a tropoelastin polypeptide or bioactive fragment thereof, wherein said effective amount is sufficient to promote adhesion of endothelial cells. The tropoelastin polypeptide or bioactive fragment thereof, has one or more of the biological activities of native tropoelastin.

In one embodiment, the method of promoting adhesion of endothelial cells is an in vitro method. In another embodiment, the method of promoting adhesion of endothelial cells is an in vivo method.

In one embodiment, the tropoelastin polypeptide or bioactive fragment thereof comprises an amino acid sequence at least 80% identical to SEQ ID NO: 2, SEQ ID NO: 3, SEQ ID NO: 4, SEQ ID NO: 5, or SEQ ID NO: 6. In another embodiment, the tropoelastin polypeptide, or bioactive fragment thereof comprises an amino acid sequence identical to SEQ ID NO: 2, SEQ ID NO: 3, SEQ ID NO: 4, SEQ ID NO: 5, or SEQ ID NO: 6. In still another embodiment, the composition consists essentially of an amino acid sequence at least 80% identical to SEQ ID NO: 2, SEQ ID NO: 3, SEQ ID NO: 4, SEQ ID NO: 5, or SEQ ID NO: 6. In yet another embodiment, the composition consists essentially of at least one repeat of a bioactive fragment represented in SEQ ID NO: 5. In another embodiment, the composition consists essentially of a bioactive fragment represented in SEQ ID NO: 6. In still another embodiment, said tropoelastin polypeptide, or bioactive fragment thereof, comprises an amino acid sequence encodable by a nucleic acid that hybridizes under stringent conditions, including a wash step of 0.2× SSC at 65° C., to a nucleic acid sequence represented in SEQ ID NO: 1. In any of the foregoing, the composition comprises or consists essentially of a tropoelastin polypeptide, or bioactive fragment thereof that retains one or more of the biological activities of native tropoelastin. Exemplary biological/functional activities of native tropoelastin that are retained by the tropoelastin polypeptides, or bioactive fragments thereof, for use in the methods and devices of the invention include, but are not limited to: (i) promotes adhesion of endothelial cells in vitro; (ii) promotes adhesion of endothelial cells in vivo; (iii) promotes adhesion of human aortic endothelial cells (HuAEC) in vitro; (iv) promotes adhesion of human aortic smooth muscle cells (huAoSMC) in vitro; (v) promotes migration of endothelial cells in vitro; (vi) promotes migration of human aortic endothelial cells (H-huAEC) in vitro; (vii) promotes adhesion of A2058 human melanoma cells in vitro; (viii) promotes migration of A2058 human melanoma cells in vitro; (ix) promotes adhesion of human microvessel endothelial cells (HMVEC) in vitro.

In another embodiment, the tropoelastin polypeptide, or bioactive fragment thereof, is covalently attached to a device. Exemplary devices are made of or coated with metal, silicone, dacron, plastic, or polytetrafluoroethylene (PTFE). Exemplary metal devices include stainless steel devices. An effective amount of the tropoelastin polypeptide, or bioactive fragment thereof, is attached to the device and the effective amount is sufficient to promote adhesion of endothelial cells to the device.

In a second aspect, the invention promotes a method of promoting migration of endothelial cells. The method comprises contacting said endothelial cells with an amount of a composition comprising an effective amount of a tropoelastin polypeptide, or bioactive fragment thereof, wherein said effective amount is sufficient to promote migration of endothelial cells. The tropoelastin polypeptide, or bioactive fragment thereof, has one or more of the biological activities of native tropoelastin.

In one embodiment, the method of promoting migration of endothelial cells is an in vitro method. In another embodiment, the method of promoting migration of endothelial cells is an in vivo method.

In one embodiment, the tropoelastin polypeptide, or bioactive fragment thereof, comprises an amino acid sequence at least 80% identical to SEQ ID NO: 2, SEQ ID NO: 3, SEQ ID NO: 4, SEQ ID NO: 5, or SEQ ID NO: 6. In another embodiment, the tropoelastin polypeptide, or bioactive fragment thereof, comprises an amino acid sequence identical to SEQ ID NO: 2, SEQ ID NO: 3, SEQ ID NO: 4, SEQ ID NO: 5, or SEQ ID NO: 6. In still another embodiment, the composition consists essentially of an amino acid sequence at least 80% identical to SEQ ID NO: 2, SEQ ID NO: 3, SEQ ID NO: 4, SEQ ID NO: 5, or SEQ ID NO: 6. In yet another embodiment, the composition consists essentially of at least one repeat of a bioactive fragment represented in SEQ ID NO: 5. In another embodiment, the composition consists essentially of a bioactive fragment represented in SEQ ID NO: 6. In still another embodiment, said tropoelastin polypeptide, or bioactive fragment thereof, comprises an amino acid sequence encodable by a nucleic acid that hybridizes under stringent conditions, including a wash step of 0.2× SSC at 65° C., to a nucleic acid sequence represented in SEQ ID NO: 1. In any of the foregoing, the composition comprises or consists essentially of a tropoelastin polypeptide, or bioactive fragment thereof, that retains one or more of the biological activities of native tropoelastin. Exemplary biological/functional activities of native tropoelastin that are retained by the tropoelastin polypeptides, or bioactive fragments thereof, for use in the methods and devices of the invention include, but are not limited to: (i) promotes adhesion of endothelial cells in vitro; (ii) promotes adhesion of endothelial cells in vivo; (iii) promotes adhesion of human aortic endothelial cells (HuAEC) in vitro; (iv) promotes adhesion of human aortic smooth muscle cells (HuAoSMC) in vitro; (v) promotes migration of endothelial cells in vitro; (vi) promotes migration of human aortic endothelial cells (HuAEC) in vitro; (vii) promotes adhesion of A2058 human melanoma cells in vitro; (viii) promotes migration of A2058 human melanoma cells in vitro; (ix) promotes adhesion of human microvessel endothelial cells (HMVEC) in vitro.

In another embodiment, the tropoelastin polypeptide, or bioactive fragment thereof, is covalently attached to a device. Exemplary devices are made of or coated with metal, plastic, Dacron, PTFE, silicone, or plastic. Exemplary metal devices include stainless steel devices. An effective amount of the tropoelastin polypeptide, or bioactive fragment thereof, is attached to the device and the effective amount is sufficient to promote migration of endothelial cells to the device.

In a third aspect, the invention provides a method of promoting adhesion of endothelial cells to a device. The method comprises contacting said endothelial cells with a device. The device comprises a composition comprising an effective amount of a tropoelastin polypeptide, or bioactive fragment thereof, and the tropoelastin or bioactive fragment thereof is covalently attached to the device. An effective amount of the tropoelastin polypeptide, or bioactive fragment thereof, is attached to the device and the effective amount is sufficient to promote adhesion of endothelial cells to the device.

In one embodiment, the method is an in vitro method. In another embodiment, the method is an in vivo method.

In one embodiment, the device is a metal device, for example, a stainless steel device. In another embodiment, the device is made from or coated with plastic, silicone, PTFE, or dacron. In one embodiment, the device is selected from a catheter, stent, shunt, wire, or other intraluminal device. In another embodiment, the device is selected from a pacemaker, cardioverter-defibrillator, artificial valve, ventricular assist device, vascular graft, nasogastric tube, ventilator tube, or chest tube.

In one embodiment, the tropoelastin polypeptide, or bioactive fragment thereof, comprises an amino acid sequence at least 80% identical to SEQ ID NO: 2, SEQ ID NO: 3, SEQ ID NO: 4, SEQ ID NO: 5, or SEQ ID NO: 6. In another embodiment, the tropoelastin polypeptide, or bioactive fragment thereof, comprises an amino acid sequence identical to SEQ ID NO: 2, SEQ ID NO: 3, SEQ ID NO: 4, SEQ ID NO: 5, or SEQ ID NO: 6. In still another embodiment, the composition consists essentially of an amino acid sequence at least 80% identical to SEQ ID NO: 2, SEQ ID NO: 3, SEQ ID NO: 4, SEQ ID NO: 5, or SEQ ID NO: 6. In yet another embodiment, the composition consists essentially of at least one repeat of a bioactive fragment represented in SEQ ID NO: 5. In another embodiment, the composition consists essentially of a bioactive fragment represented in SEQ ID NO: 6. In still another embodiment, said tropoelastin polypeptide, or bioactive fragment thereof, comprises an amino acid sequence encodable by a nucleic acid that hybridizes under stringent conditions, including a wash step of 0.2× SSC at 65° C., to a nucleic acid sequence represented in SEQ ID NO: 1. In any of the foregoing, the composition comprises or consists essentially of a tropoelastin polypeptide, or bioactive fragment thereof, that retains one or more of the biological activities of native tropoelastin. Exemplary biological/functional activities of native tropoelastin that are retained by the tropoelastin polypeptides, or bioactive fragments thereof, for use in the methods and devices of the invention include, but are not limited to: (i) promotes adhesion of endothelial cells in vitro; (ii) promotes adhesion of endothelial cells in vivo; (iii) promotes adhesion of human aortic endothelial cells (HuAEC) in vitro; (iv) promotes adhesion of human aortic smooth muscle cells (HuAoSMC) in vitro; (v) promotes migration of endothelial cells in vitro; (vi) promotes migration of human aortic endothelial cells (HuAEC) in vitro; (vii) promotes adhesion of A2058 human melanoma cells in vitro; (viii) promotes migration of A2058 human melanoma cells in vitro; (ix) promotes adhesion of human microvessel endothelial cells (HMVEC) in vitro.

In a fourth aspect, the invention provides a method for the treatment or prophylaxis of restenosis. The method comprises administering an amount of a composition comprising an amount of tropoelastin, or a bioactive fragment thereof, effective to treat or prophylactically treat restenosis. The tropoelastin, or bioactive fragment thereof, is covalently attached to a device, and administering said composition promotes adhesion of endothelial cells to said device, thereby treating or preventing restenosis.

In one embodiment, the method is performed following angioplasty, catheterization, stenting, surgery, or other interventional therapy. In another embodiment, the method is performed concomitantly with angioplasty, catheterization, stenting, surgery, or other interventional therapy. In still another embodiment, the same device used to prevent the occlusion is also coated according to the invention in order to prevent restenosis.

In one embodiment, one or more other agents are concurrently or concomitantly administered as part of a treatment regimen appropriate for the particular cardiovascular or occlusive vessel condition.

In one embodiment, the device is selected from a stent, catheter, shunt, wire, or other intraluminal device. In one embodiment, the device is a metal device, for example, a stainless steel device.

In one embodiment, the method comprises administering said device intravascularly or intraluminally to a site of cell damage within a body vessel. In another embodiment, the body vessel is selected from any of artery, vein, ureter, common bile duct, pancreatic duct, kidney duct, esophagus, trachea, urethra, bladder, uterus, ovarian duct, Fallopian tube, vas deferens, prostatic duct, or lymphatic duct.

In one embodiment, the tropoelastin polypeptide, or bioactive fragment thereof, comprises an amino acid sequence at least 80% identical to SEQ ID NO: 2, SEQ ID NO: 3, SEQ ID NO: 4, SEQ ID NO: 5, or SEQ ID NO: 6. In another embodiment, the tropoelastin polypeptide, or bioactive fragment thereof, comprises an amino acid sequence identical to SEQ ID NO: 2, SEQ ID NO: 3, SEQ ID NO: 4, SEQ ID NO: 5, or SEQ ID NO: 6. In still another embodiment, the composition consists essentially of an amino acid sequence at least 80% identical to SEQ ID NO: 2, SEQ ID NO: 3, SEQ ID NO: 4, SEQ ID NO: 5, or SEQ ID NO: 6. In yet another embodiment, the composition consists essentially of at least one repeat of a bioactive fragment represented in SEQ ID NO: 5. In another embodiment, the composition consists essentially of a bioactive fragment represented in SEQ ID NO: 6, In still another embodiment, said tropoelastin polypeptide, or bioactive fragment thereof, comprises an amino acid sequence encodable by a nucleic acid that hybridizes under stringent conditions, including a wash step of 0.2× SSC at 65° C., to a nucleic acid sequence represented in SEQ ID NO: 1. In any of the foregoing, the composition comprises or consists essentially of a tropoelastin polypeptide, or bioactive fragment thereof, that retains one or more of the biological activities of native tropoelastin. Exemplary biological/functional activities of native tropoelastin that are retained by the tropoelastin polypeptides, or bioactive fragments thereof, for use in the methods and devices of the invention include, but are not limited to: (i) promotes adhesion of endothelial cells in vitro; (ii) promotes adhesion of endothelial cells in vivo; (iii) promotes adhesion of human aortic endothelial cells (HuAEC) in vitro; (iv) promotes adhesion of human aortic smooth muscle cells (HuAoSMC) in vitro; (v) promotes migration of endothelial cells in vitro; (vi) promotes migration of human aortic endothelial cells (HuAEC) in vitro; (vii) promotes adhesion of A2058 human melanoma cells in vitro; (viii) promotes migration of A2058 human melanoma cells in vitro; (ix) promotes adhesion of human microvessel endothelial cells (HMVEC) in vitro.

In a fifth aspect, the invention provides a method for the treatment or prophylaxis of thrombosis. The method comprises administering an amount of a composition comprising an amount of tropoelastin, or a bioactive fragment thereof, effective to treat or prophylactically treat thrombosis. The tropoelastin, or bioactive fragment thereof, is covalently attached to a device, and administering said composition promotes adhesion of endothelial cells to said device, thereby treating or preventing thrombosis.

In one embodiment, the method is performed following angioplasty, catheterization, stenting, surgery, or other interventional therapy. In another embodiment, the method is performed concomitantly to angioplasty, catheterization, stenting or other interventional therapy. In still another embodiment, the same device used to prevent the occlusion is also coated according to the invention to prevent thrombosis.

In one embodiment, one or more other agents are concurrently or concomitantly administered as part of a treatment regimen appropriate for the particular cardiovascular or occlusive vessel condition.

In one embodiment, the device is selected from a stent, catheter, shunt, wire, or other intraluminal device. In another embodiment, the device is selected from a pacemaker, cardioverter-defibrillator, artificial valve, ventricular assist device, vascular graft, nasogastric device, ventilator tube, or chest tube. In one embodiment, the device is a metal device. In another embodiment, the metal device is a stainless steel device. In another embodiment, the device is made of or coated with plastic, silicone, Dacron, or PTFE.

In one embodiment, the method comprises administering said device intravascularly or intraluminally to a site of cell damage within a body vessel. In another embodiment, the body vessel is selected from any of artery, vein, ureter, common bile duct, pancreatic duct, kidney duct, esophagus, trachea, urethra, bladder, uterus, ovarian duct, Fallopian tube, vas deferens, prostatic duct, or lymphatic duct.

In one embodiment, the tropoelastin polypeptide, or bioactive fragment thereof, comprises an amino acid sequence at least 80% identical to SEQ ID NO: 2, SEQ ID NO: 3, SEQ ID NO: 4, SEQ ID NO: 5, or SEQ ID NO: 6. In another embodiment, the tropoelastin polypeptide, or bioactive fragment thereof, comprises an amino acid sequence identical to SEQ ID NO: 2, SEQ ID NO: 3, SEQ ID NO: 4, SEQ ID NO: 5, or SEQ ID NO: 6. In still another embodiment, the composition consists essentially of an amino acid sequence at least 80% identical to SEQ ID NO: 2, SEQ ID NO: 3, SEQ ID NO: 4, SEQ ID NO: 5, or SEQ ID NO: 6. In yet another embodiment, the composition consists essentially of at least one repeat of a bioactive fragment represented in SEQ ID NO: 5. In another embodiment, the composition consists essentially of a bioactive fragment represented in SEQ ID NO: 6. In still another embodiment, said tropoelastin polypeptide, or bioactive fragment thereof, comprises an amino acid sequence encodable by a nucleic acid that hybridizes under stringent conditions, including a wash step of 0.2× SSC at 65° C., to a nucleic acid sequence represented in SEQ ID NO: 1. In any of the foregoing, the composition comprises or consists essentially of a tropoelastin polypeptide, or bioactive fragment thereof, that retains one or more of the biological activities of native tropoelastin. Exemplary biological/functional activities of native tropoelastin that are retained by the tropoelastin polypeptides, or bioactive fragments thereof, for use in the methods and devices of the invention include, but are not limited to: (i) promotes adhesion of endothelial cells in vitro; (ii) promotes adhesion of endothelial cells in vivo; (iii) promotes adhesion of human aortic endothelial cells (HuAEC) in vitro; (iv) promotes adhesion of human aortic smooth muscle cells (HuAoSMC) in vitro; (v) promotes migration of endothelial cells in vitro; (vi) promotes migration of human aortic endothelial cells (HuAEC) in vitro; (vii) promotes adhesion of A2058 human melanoma cells in vitro; (viii) promotes migration of A2058 human melanoma cells in vitro; (ix) promotes adhesion of human microvessel endothelial cells (HMVEC) in vitro.

In a sixth aspect, the invention provides a device. The device comprises a tropoelastin polypeptide, or a bioactive fragment thereof. The tropoelastin polypeptide, or bioactive fragment thereof, is covalently attached to said device. The device comprises an amount of said tropoelastin polypeptide, or bioactive fragment thereof, effective to promote adhesion of endothelial cells to said device.

In one embodiment, the device, is a metal device. In another embodiment, the metal device is a stainless steel device. In another embodiment, the device is selected from a catheter, stent, shunt, wire, or other intraluminal device. In another embodiment, the device is selected from a pacemaker, cardioverter-defibrillator, artificial valve, ventricular assist device, vascular graft, nasogastric tube, ventilator tube, or chest tube.

In a seventh aspect, the invention provides a method for screening to identify bioactive fragments of tropoelastin that retain one or more of the biological activities of tropoelastin. In one embodiment, the screening method is performed using endothelial cells or endothelial progenitor cells in culture to identify and/or characterize bioactive fragments of tropoelastin that retain the ability to promote adhesion and/or migration of endothelial cells in vitro.

In one embodiment, the endothelial cells in culture are mammalian cells. In another embodiment, the endothelial cells in culture are mouse cells or rat cells. In another embodiment, the endothelial cells in culture are pig cells. In still another embodiment, the endothelial cells in culture are human cells. In another embodiment, the endothelial cells are human microvessel endothelial cells. In yet another embodiment, the endothelial cells are human aortic endothelial cells (HuAEC).

In one embodiment, the screening method is a high-throughput screening method.

The invention contemplates combinations of any of the foregoing aspects and embodiments. In one embodiment of any of the foregoing, the invention provides a method of promoting adhesion of endothelial cells. In one embodiment, the invention provides a method of promoting adhesion of endothelial stem cells.

In certain embodiments of any of the foregoing, the invention provides methods for promoting adhesion of endothelial cells or endothelial stem cells, for example, methods of promoting adhesion to a device. The invention further provides devices to which a tropoelastin polypeptide or bioactive fragment is covalently attached or appended. In certain embodiments, the adhesion of endothelial cells or endothelial stem cells is sufficient such that adherent cells are retained on the device under physiologically relevant flow rates and/or pressures. By physiologically relevant is meant that cells that adhere to a device bearing tropoelastin or a bioactive fragment thereof are retained on the device at flow rates and/or pressures equivalent to venous and/or arterial flow rates and/or pressures. For embodiments in which a device is place intraluminally into a vessel other than an artery or vein, the term physiologically relevant refers to the pressure and/or fluid flow rates equivalent to those experienced in the particular vessel (e.g., vas deferens, urethra, ureter, prostatic duct, bile duct, etc).

In any of the foregoing, tropoelastin or bioactive fragments thereof may be used alone to promote adhesion and/or migration of endothelial cells. Alternatively, tropoelastin or bioactive fragments thereof may be used in combination with one or more other therapeutic regimens appropriate to the particular condition being treated. Furthermore, tropoelastin, or bioactive fragments thereof, may be used alone or in combination with another adhesion promoting agent. In one embodiment, adhesion of endothelial cells is promoted using a device coated with tropoelastin, or a bioactive fragment thereof. In another embodiment, the device is co-coated with both tropoelastin, or a bioactive fragment thereof, and anti-CD34 antibody.

In any of the foregoing, devices of the invention to which tropoelastin or one or more bioactive fragments thereof are attached can be made of or coated with metal, plastic, silicone, dacron, poly ethane, polypropylene, PTFE, or derivatives thereof. Attachment can be covalently, for example via a polysaccharide linkage. Alternatively, attachment can be via crosslinking using commonly employed crosslinking agents.

In certain embodiments of any of the foregoing, the methods, compositions, and devices of the invention can be used in the prophylaxis or treatment of thrombosis. In certain embodiments, devices coated with the subject polypeptides may be non-thrombogenic. In other embodiments, devices coated with the subject polypeptides may be anti-thrombogenic. In still other embodiments, the devices coated with the subject polypeptides will be substantially less thrombogenic than similar uncoated devices. Regardless of whether a particular coated device has anti-thrombogenic properties or is simply non-thrombogenic, coated devices according to the present invention decrease or prevent thrombosis in comparison to alternative interventional therapies.

The practice of the present invention will employ, unless otherwise indicated, conventional techniques of cell biology, cell culture, molecular biology, transgenic biology, microbiology, virology, recombinant DNA, and immunology, which are within the skill of the art. Such techniques are described in the literature. See, for example, Molecular Cloning: A Laboratory Manual, 3rd Ed., ed. by Sambrook and Russell. (Cold Spring Harbor Laboratory Press: 2001); the treatise, Methods In Enzymology (Academic Press, Inc., N.Y.); Using Antibodies, Second Edition by Harlow and Lane, Cold Spring Harbor Press, New York, 1999; Current Protocols in Cell Biology, ed. by Bonifacino, Dasso, Lippincott-Schwartz, Harford, and Yamada, John Wiley and Sons, Inc., New York, 1999.

Other features and advantages of the invention will be apparent from the following detailed description, and from the claims.

Figure 1:
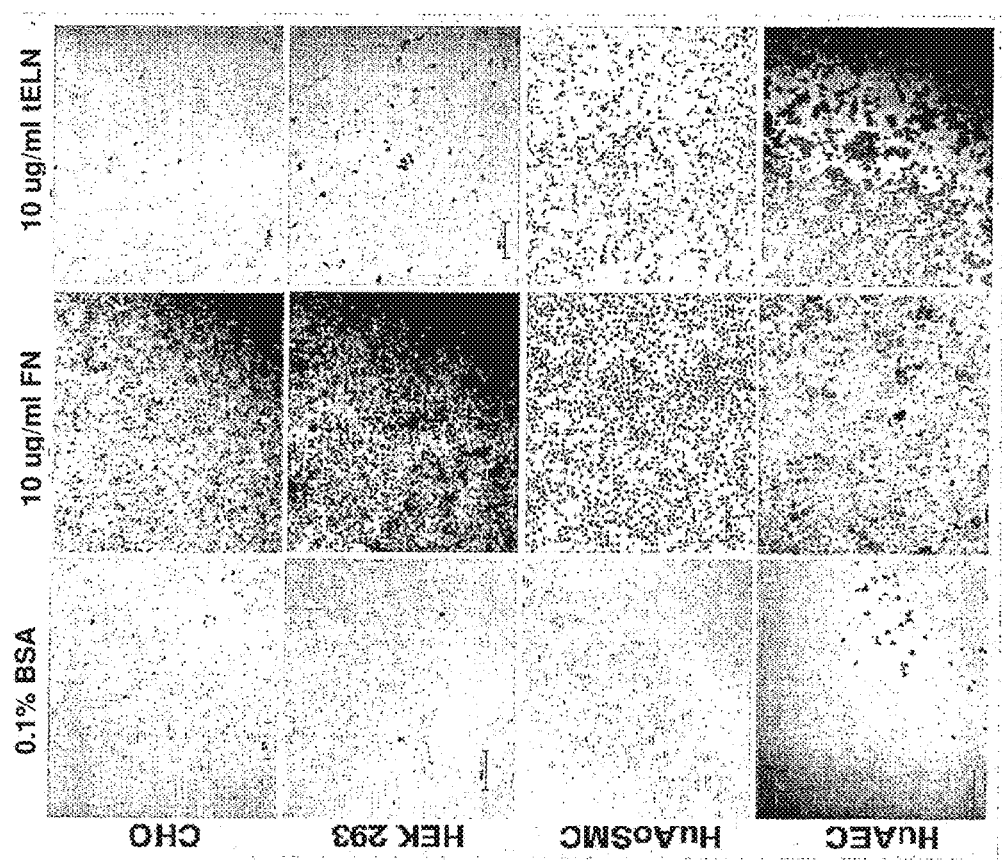
FIG. 1 shows the effect of fibronectin and tropoelastin on the adhesion of CHO cells, human embryonic kidney cells (HK 293), human aortic smooth muscle cells (HuAoSMC), and human aortic endothelial cells (HuAEC). For each cell type, cell adhesion was measured in culture dishes coated with either fibronectin or recombinant human tropoelastin. Note that endothelial cells, and to a lesser extent smooth muscle cells, adhere to culture dishes coated with tropoelastin. In comparison, CHO cells and HEK 293 cells adhere to culture dishes coated with fibronectin but not to culture dishes coated with tropoelastin.

DETAILED DESCRIPTION OF THE INVENTION (i) Overview

Biological properties of elastin and the elastin-signaling pathway are provided in Li et al. (1998) *Journal of Clinical Investigation* 102: 1783-1787; Li et al. (1998) *Nature* 393: 276-280; Karnik et at, (2003) *Matrix Biology* 22: 409-425; Karnik et al. (2003) *Development* 130: 411-423; and Brooke et al. (2003) *Trends in Cardiovascular Medicine* 13: 176-181, the disclosures of which are hereby incorporated by reference in their entirety. Briefly, these and other references demonstrated the effect of modulating elastin signaling on smooth muscle cells and vascular smooth muscle cells. However, until now, the utility of tropoelastin, and bioactive fragments thereof, to modulate the adhesion and migration of endothelial cells was not recognized.

Based on the findings disclosed in the present application, tropoelastin, and bioactive fragments thereof, can be used to promote the adhesion and/or migration of endothelial cells. This finding allows the development of in vitro methods of using tropoelastin, or bioactive fragments thereof, either alone or in association with a device. Exemplary in vitro uses include screening assays to identify and/or characterize fragments of tropoelastin or peptidomimetics that retain one or more of the functional activities of native (e.g., full length) tropoelastin.

This finding also allows for the development of in vivo methods of using tropoelastin, or bioactive fragments thereof. An exemplary in vivo use is to promote the adhesion of endothelial cells to a device to which tropoelastin, or a bioactive fragment thereof has been covalently attached. In an in vivo context, endothelization of implantable devices (e.g., prior to or following placement in a patient) can help prevent or reduce restenosis and/or thrombosis. The ability to promote endothelialization of implantable devices is a significant advance that will increase the potential efficacy of any of a number of interventional approaches. Given that currently used and contemplated implantable devices and interventional approaches pose a significant risk of thrombosis and/or restenosis, the methods and compositions of the present invention will substantially reduce the risks involved with these procedures, thereby increasing their safety and efficacy.

(ii) Definitions

For convenience, certain terms employed in the specification, examples, and appended claims are collected here. Unless defined otherwise, all technical and scientific terms used herein have the same meaning as commonly understood by one of ordinary skill in the art to which this invention belongs.

The articles "a" and "an" are used herein to refer to one or to more than one (i.e., to at least one) of the grammatical object of the article. By way of example, "an element" means one element or more than one element.

As used herein, "protein" is a polymer consisting essentially of any of the 20 amino acids. Although "polypeptide" is often used in reference to relatively large polypeptides, and "peptide" is often used in reference to small polypeptides, usage of these terms in the art overlaps and is varied.

The terms "peptide(s)" "protein(s)" and "polypeptide(s)" are used interchangeably herein.

The terms "polynucleotide sequence" and "nucleotide sequence" are also used interchangeably herein.

"Recombinant," as used herein, means that a protein is derived from a prokaryotic or eukaryotic expression system.

The term "wildtype" refers to the naturally-occurring polynucleotide sequence encoding a protein, or a portion thereof, or protein sequence, or portion thereof, respectively, as it normally exists in vivo.

The term "mutant" refers to any change in the genetic material of an organism, in particular a change (i.e., deletion, substitution, addition, or alteration) in a wild type polynucleotide sequence or any change in a wild type protein. The term "variant" is used interchangeably with "mutant". Although it is often assumed that a change in the genetic material results in a change of the function of the protein, the terms "mutant" and "variant" refer to a change in the sequence of a wildtype protein regardless of whether that change alters the function of the protein (e.g., increases, decreases, imparts a new function), or whether that change has no effect on the function of the protein (e.g., the mutation or variation is silent).

As used herein, the term "nucleic acid" refers to polynucleotides such as deoxyribonucleic acid (DNA), and, where appropriate, ribonucleic acid (RNA). The term should also be understood to include, as equivalents, analogs of RNA or DNA made from nucleotide analogs, and, as applicable to the embodiment being described, single (sense or antisense) and double-stranded polynucleotides.

As used herein, the term "gene" or "recombinant gene" refers to a nucleic acid comprising an open reading frame encoding a polypeptide, including both exon and (optionally) intron sequences.

As used herein, the term "vector" refers to a nucleic acid molecule capable of transporting another nucleic acid to which it has been linked. Preferred vectors are those capable of autonomous replication and/or expression of nucleic acids to which they are linked. Vectors capable of directing the expression of genes to which they are operatively linked are referred to herein as "expression vectors".

A polynucleotide sequence (DNA, RNA) is "operatively linked" to an expression control sequence when the expression control sequence controls and regulates the transcription and translation of that polynucleotide sequence. The term "operatively linked" includes having an appropriate start signal (e.g., ATG) in front of the polynucleotide sequence to be expressed, and maintaining the correct reading frame to permit expression of the polynucleotide sequence under the control of the expression control sequence, and production of the desired polypeptide encoded by the polynucleotide sequence.

"Transcriptional regulatory sequence" is a generic term used throughout the specification to refer to nucleic acid sequences, such as initiation signals, enhancers, and promoters, which induce or control transcription of protein coding sequences with which they are operably linked. In some examples, transcription of a recombinant gene is under the control of a promoter sequence (or other transcriptional regulatory sequence) which controls the expression of the recombinant gene in a cell-type in which expression is intended. It will also be understood that the recombinant gene can be under the control of transcriptional regulatory sequences Which are the same or which are different from those sequences which control transcription of the naturally-occurring form of a protein.

As used herein, the term "tissue-specific promoter" means a nucleic acid sequence that serves as a promoter, i.e., regulates expression of a selected nucleic acid sequence operably linked to the promoter, and which affects expression of the selected nucleic acid sequence in specific cells of a tissue, such as cells of neural origin, e.g. neuronal cells. The term also covers so-called "leaky" promoters, which regulate expression of a selected nucleic acid primarily in one tissue, but cause expression in other tissues as well.

"Identity" refers to sequence similarity between two peptides or between two nucleic acid molecules. Identity can be determined by comparing a position in each sequence which may be aligned for purposes of comparison. When a position in the compared sequence is occupied by the same base or amino acid, then the molecules are identical at that position. A degree of identity between sequences is a function of the number of matching positions shared by the sequences.

A "chimeric protein" or "fusion protein" is a fusion of a first amino acid sequence encoding a polypeptide with a second amino acid sequence defining a domain (e.g. polypeptide portion) foreign to and not substantially homologous with any domain of the first polypeptide. A chimeric protein may present a foreign domain which is found (albeit in a different protein) in an organism which also expresses the first protein, or it may be an "interspecies", "intergenic", etc. fusion of protein structures expressed by different kinds of organisms.

The "non-human animals" of the invention include mammals such as rats, mice, rabbits, sheep, cats, dogs, cows, pigs, and non-human primates.

The term "isolated" as used herein with respect to nucleic acids, such as DNA or RNA, refers to molecules separated from other DNAs, or RNAs, respectively, that are present in the natural source of the macromolecule. The term isolated as used herein also refers to a nucleic acid or peptide that is substantially free of cellular material or culture medium when produced by recombinant DNA techniques, or chemical precursors or other chemicals when chemically synthesized. Moreover, an "isolated nucleic acid" is meant to include nucleic acid fragments which are not naturally occurring as fragments and would not be found in the natural state.

As used herein, "proliferating" and "proliferation" refer to cells undergoing mitosis.

The phrases "parenteral administration" and "administered parenterally" as used herein means modes of administration other than enteral and topical administration, usually by injection, and includes, without limitation, intravenous, intravascular, intramuscular, intraarterial, intrathecal, intraventricular, intracapsular, intraorbital, intracardiac, intradermal, intraperitoneal, transtracheal, subcutaneous, subcuticular, intraarticular, subcapsular, subarachnoid, intraspinal, and intrasternal injection and infusion.

The phrases "systemic administration," "administered systemically," "peripheral administration" and "administered peripherally" as used herein mean the administration of a compound, drug or other material other than directly into the central nervous system, such that it enters the animal's system and, thus, is subject to metabolism and other like processes, for example, subcutaneous administration.

The phrase "effective amount" as used herein means that the amount of one or more agent, material, or composition comprising one or more agents as described herein which is effective for producing some desired effect in a subject.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically acceptable carrier" as used herein means a pharmaceutically acceptable material, composition or vehicle, such as a liquid or solid filler, diluent, excipient, solvent or encapsulating material, involved in carrying or transporting the subject agents from one organ, or portion of the body, to another organ, or portion of the body. Each carrier must be "acceptable" in the sense of being compatible with the other ingredients of the formulation.

Functional equivalents of a polypeptide, a polypeptide fragment, or a variant polypeptide are those polypeptides that retain a biological and/or a immunological activity of the native or naturally-occurring polypeptide. Immunological activity refers to the ability to induce the production of an antibody against an antigenic epitope possessed by a native polypeptide; biological activity refers to a function, either inhibitory or stimulatory, caused by the particular native polypeptide that excludes immunological activity. In the context of the present invention, exemplary biological activities include, but are not limited to: (i) promotes adhesion of endothelial cells in vitro; (ii) promotes adhesion of endothelial cells in vivo; (iii) promotes adhesion of human aortic endothelial cells (HuAEC) in vitro; (iv) promotes adhesion of human aortic smooth muscle cells (HuAoSMC) in vitro; (v) promotes migration of endothelial cells in vitro; (vi) promotes migration of human aortic endothelial cells (HuAEC) in vitro; (vii) promotes adhesion of A2058 human melanoma cells in vitro; (viii) promotes migration of A2058 human melanoma cells in vitro; (ix) promotes adhesion of human microvessel endothelial cells (HMVEC) in vitro. Further exemplary biological activities include the ability to bind to a particular receptor, the ability to activate transcription of a particular gene, the ability to inhibit transcription of a particular gene, the ability to associate (e.g., directly or indirectly associate) with a particular cofactor, the ability to promote signaling via a particular signal transduction pathway, and the ability to inhibit signaling via another particular signal transduction pathway.

Variant nucleic acid or amino acid sequences may be full length or other than full length. Variants of the nucleic acids or proteins of the invention include, but are not limited to, molecules comprising regions that are identical to the nucleic acids or proteins of the invention. In various embodiments, the variants are at least about 60%, 65%, 70%, 75%, 80%, 83%, 85%, 90%, 95%, 97%, 98%, 99%, or greater than 99% identical to a nucleic acid or amino acid sequence of identical size or when compared to an aligned sequence in which the alignment is done by a computer homology program known in the art, or whose encoding nucleic acid is capable of hybridizing to the complement of a sequence encoding the aforementioned proteins under stringent, moderately stringent, or low stringent conditions. Variants can also be described with respect to how many residues differ between polypeptides. For example, a variant may differ from a given polypeptide sequence at one of six amino acid residues, at two of six amino acid residues, or at three of six amino acid residues.

A "homologous nucleic acid sequence" or "homologous amino acid sequence," or variations thereof, refer to sequences characterized by a degree of identity at the nucleotide level or amino acid level as discussed above. Homologous nucleotide sequences encode those sequences coding for isoforms of a particular sequence. Isoforms can be expressed in different tissues of the same organism as a result of, for example, alternative splicing of RNA. Alternatively, different genes can encode isoforms. Homologous nucleotide sequences include nucleotide sequences encoding a polypeptide from other species, including, but not limited to: vertebrates, and thus can include, e.g., human, frog, mouse, rat, rabbit, dog, cat, cow, horse, and other organisms. Homologous nucleotide sequences also include, but are not limited to, naturally occurring allelic variations and mutations of the nucleotide sequences set forth herein. A homologous nucleotide sequence does not, however, include the exact nucleotide sequence encoding a particular protein. Homologous nucleic acid sequences include those nucleic acid sequences that encode conservative amino acid substitutions (see below).

As used herein, certain exemplary compositions comprise, consist of, or consist essentially of all or a portion of a tropoelastin amino acid or nucleic acid sequence. As used herein, "tropoelastin" refers to all or a portion of a protein encodable by all or a portion of an elastin gene. The term also refers to splice and proteolytic products of an elastin gene. The term also refers to tropoelastin protein and protein fragments whether encoded by an elastic gene, synthetically produced, or purified from a naturally occurring human or animal source of elastin. The term tropoelastin, or bioactive fragment thereof, will be used throughout the application to refer to any of the foregoing elastin-based compositions. An exemplary nucleic acid sequence of a human tropoelastin is represented in SEQ ID NO: 1 and an amino acid sequence is represented in SEQ ID NO: 2. Further exemplary tropoelastin amino acid sequences are represented in SEQ ID NO: 3 and 4. Tropoelastin is able to stimulate elastin signaling, and stimulation of elastin signaling has one or more of the following functional consequences including, but not limited to: (i) promotes adhesion of endothelial cells in vitro; (ii) promotes adhesion of endothelial cells in vivo; (iii) promotes adhesion of human aortic endothelial cells (HuAEC) in vitro; (iv) promotes adhesion of human aortic smooth muscle cells (HuAoSMC) in vitro; (v) promotes migration of endothelial cells in vitro; (vi) promotes migration of human aortic endothelial cells (HuAEC) in vitro; (vii) promotes adhesion of A2058 human melanoma cells in vitro; (viii) promotes migration of A2058 human melanoma cells in vitro; (ix) promotes adhesion of human microvessel endothelial cells (HMVEC) in vitro. Tropoelastin polypeptides, or bioactive fragments thereof, for use in the methods and devices of the present invention possess one or more of the foregoing functional activities of native tropoelastin. In one embodiment, the adhesion promoted by tropoelastin, or a bioactive fragment, is dependant (in whole or in part) on integrin $\alpha_v\beta_3$.

In addition to full length tropoelastin, bioactive fragments of tropoelastin can stimulate elastin signaling. By bioactive fragment is meant that a given portion of the protein maintains one or more of the functional attributes of the full length protein. In the context of the present invention, a bioactive fragment of tropoelastin retains all or a portion of the ability to promote elastin signaling and thus results in one or more of the functional consequences of elastin signaling including, but not limited to: (i) promotes adhesion of endothelial cells in vitro; (ii) promotes adhesion of endothelial cells in vivo; (iii) promotes adhesion of human aortic endothelial cells (HuAEC) in vitro; (iv) promotes adhesion of human aortic smooth muscle cells (HuAoSMC) in vitro; (v) promotes migration of endothelial cells in vitro; (vi) promotes migration of human aortic endothelial cells (HuAEC) in vitro; (vii) promotes adhesion of A2058 human melanoma cells in vitro; (viii) promotes migration of A2058 human melanoma cells in vitro; (ix) promotes adhesion of human microvessel endothelial cells (HMVEC) in vitro. An exemplary bioactive fragment of tropoelastin is provided in SEQ ID NO: 5. Another exemplary bioactive fragment of tropoelastin is provided in SEQ ID NO: 6. Fragments can be made by any method including synthetic methods. The invention contemplates the use not only of bioactive peptide fragments of tropoelastin, but also peptidomimetics (modified fragments). Exemplary peptidomimetics of tropoelastin are peptidomimetics of SEQ ID NO: 5 or SEQ ID NO: 6. In one embodiment, the adhesion promoted by tropoelastin, or a bioactive fragment, is dependant (in whole or in part) on integrin $\alpha_v\beta_3$.

The terms "antiproliferative agent" and "antiproliferative compound" are used interchangeably throughout the application to refer to any peptide or nonpeptide agent that inhibit proliferation. The present invention contemplates that the compositions and devices of the invention may sometimes be administered concurrently or concomitantly with other agents as part of a therapeutic treatment regimen appropriate for the particular indication being treated. One such class of agents comprises antiproliferative agents. Exemplary antiproliferative agents include, but are not limited to halogenated purine or pyrimidine analogs (e.g., fluorinated analogs), macrolids, cytoskeletal/microtubule destabilizers, radioactivity, and the like. Further non-limiting examples, of antiproliferative agents include 5-fluorouracil (5-FU); 5'-deoxy-5-fluorouridine; 5-fluorouridine, 2'-deoxy-5-fluorouridine; fluorocytosine; 5-trifluoromethyl-2'-deoxyuridine; alitretinoin (9-cis-retinoic acid); amifostine; bexarotene (4-[1-(5,6,7,8-tetrahydro-3,5,5,8,8-pentamethyl-2-naphthalenyl) ethenyl] benzoic acid); bleomycin; capecitabine (5'-deoxy-5-fluoro-cytidine); chlorambucil; cladribine; cytarabine; daunorubicin; docetaxel; doxorubicin epirubicin; estramustine; etoposide; exemestane (6-methylenandrosta-1,4-diene-3,17-dione); fludarabine; 5-fluorouracil; gemcitabine; hydroxyurea; idarubicin; irinotecan; melphalan; methotrexate; mitoxantrone; paclitaxel; pentostatin; prednimustine; streptozocin; temozolomide; teniposide; tomudex; topotecan; valrubicin (N-trifluoroacetyladriamycin-14-valerate); vinorelbine; and salts of the foregoing. Still additional examples include actinomycinD; cytochalasin D; dexamethasone; everolimus; sirolimus; tacrolimus; latrunculin A; rapamycin, and analogues thereof such as ABT-578; carvedilol; FK506; taxol; cyclosporine; camptothecin; carubicin; chlorozotocin, chromomycins, including chromomycin, A$_3$; cladribine; colchicine, combretastatin, demecolcine, denopterin, doxorubicin; dromostanolone, edatrexate enocitabine, epitiostanol, formestane, lentinan, lonidamine, melengestrol, menogaril, nogalamycin; nordihydroguaiaretic acid, olivomycins such as olivomycin A, pirarubicin, plicamycin, porfiromycin, prednimustine, puromycin; ranimustine, ristocetins such as ristocetin A; tegafur, vinblastine, vindesine, and zorubicin. For any of the foregoing antiproliferative agents, the invention similarly contemplates the use of pharmaceutically acceptable salts, esters, prodrugs, analogues and protected forms thereof which retain all or a portion of the antiproliferative activity. Another class of agents include dietary supplements. Still another class of agents include beta-blockers and other high blood pressure mediation. The invention contemplates combinatorial therapies comprising both the compositions and devices of the invention along with other therapeutic regimens appropriate to the particular condition being treated. However, in certain embodiments, the use of the compositions and devices of the invention obviates the need for all or a portion of the previously recommended or prescribed treatment regimen.

The term "appended" refers to the addition of one or more moieties to an amino acid residue. The term refers, without limitation, to the addition of any moiety to any amino acid residue. The term includes attachment of a moiety via covalent or non-covalent interactions.

The term "N-terminal amino acid residue" refers to the first amino acid residue (amino acid number 1) of a polypeptide or peptide.

The term "C-terminal amino acid residue" refers to the last amino acid residue (amino acid number n, wherein n=the total number of residues in the peptide or polypeptide) of a polypeptide or peptide.

The term "amino acid side chain" is that part of an amino acid exclusive of the —CH(NH$_2$)COOH portion, as defined by K. D. Kopple, "Peptides and Amino Acids", W. A. Benjamin Inc., New York and Amsterdam, 1966, pages 2 and 33; examples of such side chains of the common amino acids are —CH$_2$CH$_2$SCH$_3$ (the side chain of methionine), —CH$_2$(CH$_3$)—CH$_2$CH$_3$ (the side chain of isoleucine), —CH$_2$CH(CH)$_2$ (the side chain of leucine) or H-(the side chain of glycine).

In certain embodiments, the amino acids used in the application of this invention are those naturally occurring amino acids found in proteins, or the naturally occurring anabolic or catabolic products of such amino acids which contain amino and carboxyl groups. Particularly suitable amino acid side chains include side chains selected from those of the following amino acids: glycine, alanine, valine, cysteine, leucine, isoleucine, serine, threonine, methionine, glutamic acid, aspartic acid, glutamine, asparagine, lysine, arginine, proline, histidine, phenylalanine, tyrosine, and tryptophan.

The term "amino acid residue" further includes analogs, derivatives and congeners of any specific amino acid referred to herein, as well as C-terminal or N-terminal protected amino acid derivatives (e.g. modified with an N-terminal or C-terminal protecting group). For example, the present invention contemplates the use of amino acid analogs wherein a side chain is lengthened or shortened while still providing a carboxyl, amino or other reactive precursor functional group for cyclization, as well as amino acid analogs having variant side chains with appropriate functional groups). For instance, the subject compound can include an amino acid analog such as, for example, cyanoalanine, canavanine, djenkolic acid, norleucine, 3-phosphoserine, homoserine, dihydroxy-phenylalanine, 5-hydroxytryptophan, 1-methylhistidine, 3-methylhistidine, diaminopimelic acid, ornithine, or diaminobutyric acid. Other naturally occurring amino acid metabolites or precursors having side chains which are suitable herein will be recognized by those skilled in the art and are included in the scope of the present invention.

Also included are the (D) and (L) stereoisomers of such amino acid when the structure of the amino acid admits of stereoisomeric forms. The configuration of the amino acids and amino acid residues herein are designated by the appropriate symbols (D), (L) or (DL), furthermore when the configuration is not designated the amino acid or residue can have the configuration (D), (L) or (DL). It will be noted that the structure of some of the compounds of this invention includes asymmetric carbon atoms. It is to be understood accordingly that the isomers arising from such asymmetry are included within the scope of this invention. Such isomers can be obtained in substantially pure form by classical separation techniques and by sterically controlled synthesis. For the purposes of this application, unless expressly noted to the contrary, a named amino acid shall be construed to include both the (D) or (L) stereoisomers.

A "reversed" or "retro" peptide sequence as disclosed herein refers to that part of an overall sequence of covalently-bonded amino acid residues (or analogs or mimetics thereof) wherein the normal carboxyl-to amino direction of peptide bond formation in the amino acid backbone has been reversed such that, reading in the conventional left-to-right direction, the amino portion of the peptide bond precedes (rather than follows) the carbonyl portion. See, generally, Goodman, M. and Chorev, M. Accounts of Chem. Res. 1979, 12, 423.

The reversed orientation peptides described herein include (a) those wherein one or more amino-terminal residues are converted to a reversed ("rev") orientation (thus yielding a second "carboxyl terminus" at the left-most portion of the molecule), and (b) those wherein one or more carboxyl-terminal residues are converted to a reversed ("rev") orientation (yielding a second "amino terminus" at the right-most portion of the molecule). A peptide (amide) bond cannot be formed at the interface between a normal orientation residue and a reverse orientation residue.

Therefore, certain reversed peptide compounds of the invention can be formed by utilizing an appropriate amino acid mimetic moiety to link the two adjacent portions of the sequences depicted above utilizing a reversed peptide (reversed amide) bond. In case (a) above, a central residue of a diketo compound may conveniently be utilized to link structures with two amide bonds to achieve a peptidomimetic structure. In case (b) above, a central residue of a diamino compound will likewise be useful to link structures with two amide bonds to form a peptidomimetic structure.

The reversed direction of bonding in such compounds will generally, in addition, require inversion of the enantiomeric configuration of the reversed amino acid residues in order to maintain a spatial orientation of side chains that is similar to that of the non-reversed peptide. The configuration of amino acids in the reversed portion of the peptides is preferably (D), and the configuration of the non-reversed portion is preferably (L). Opposite or mixed configurations are acceptable when appropriate to optimize a binding activity.

Certain compounds of the present invention may exist in particular geometric or stereoisomeric forms. The present invention contemplates all such compounds, including cis- and trans-isomers, R- and S-enantiomers, diastereomers, (D)-isomers, (L)-isomers, the racemic mixtures thereof, and other mixtures thereof, as falling within the scope of the invention. Additional asymmetric carbon atoms may be present in a substituent such as an alkyl group. All such isomers, as well as mixtures thereof, are intended to be included in this invention.

If, for instance, a particular enantiomer of a compound of the present invention is desired, it may be prepared by asymmetric synthesis, or by derivation with a chiral auxiliary, where the resulting diastereomeric mixture is separated and the auxiliary group cleaved to provide the pure desired enantiomers. Alternatively, where the molecule contains a basic functional group, such as amino, or an acidic functional group, such as carboxyl, diastereomeric salts are formed with an appropriate optically-active acid or base, followed by resolution of the diastereomers thus formed by fractional crystallization or chromatographic means well known in the art, and subsequent recovery of the pure enantiomers.

For purposes of this invention, the chemical elements are identified in accordance with the Periodic Table of the Elements, CAS version, Handbook of Chemistry and Physics, 67th Ed., 1986-87, inside cover. Also for purposes of this invention, the term "hydrocarbon" is contemplated to include all permissible compounds having at least one hydrogen and one carbon atom. In a broad aspect, the permissible hydrocarbons include acyclic and cyclic, branched and unbranched, carbocyclic and heterocyclic, aromatic and nonaromatic organic compounds which can be substituted or unsubstituted.

(II) Exemplary Elastin-Based Composition and Methods

The present invention provides compositions, methods, and devices that can be used to promote adhesion and/or migration of endothelial cells. Specifically, the present invention provides compositions and devices comprising or consisting essentially of tropoelastin, or bioactive fragments thereof. Tropoelastin polypeptides or bioactive fragments for use in the methods, compositions, and devices of the invention retain one or more of the functional/biological activities of native tropoelastin. Exemplary biological activities include, but are not limited to, one or more of the following biological activities: (i) promotes adhesion of endothelial cells in vitro; (ii) promotes adhesion of endothelial cells in vivo; (iii) promotes adhesion of human aortic endothelial cells (HuAEC) in vitro; (iv) promotes adhesion of human aortic Smooth muscle cells (HuAoSMC) in vitro (v) promotes migration of endothelial cells in vitro; (vi) promotes migration of human aortic endothelial cells (HuAEC) in vitro; (vii) promotes adhesion of A2058 human melanoma cells in vitro; (viii) promotes migration of A2058 human melanoma cells in vitro; (ix) promotes adhesion of human microvessel endothelial cells (HMVEC) in vitro.

Polypeptides and peptide fragments: The present invention provides composition and devices comprising or consisting essentially of tropoelastin polypeptide, or a bioactive fragment thereof. Such compositions and devices can be used in the in vivo or in vitro methods of the invention.

In certain embodiments, the compositions or devices comprise a tropoelastin polypeptide, or a bioactive fragment thereof. Such polypeptides or fragments can include either a wildtype peptide sequence or a variant sequence, and variant sequences can be readily constructed and tested to ensure that the variant sequence retains one or more of the biological activities of the native polypeptide. One of skill in the art can readily make variants comprising an amino acid sequence at least 60%, 70%, 75%, 80%, 83%, 85%, 90%, 95%, 98% or 99% identical to a particular polypeptide, and identify variants that activate elastin signaling and retain one or more of the biological activities of native tropoelastin. To further illustrate, the present invention contemplates variant polypeptides comprising an amino acid sequence at least 60%, 70%, 75%, 80%, 85%, 90%, 95%, 98%, 99%, or 100% identical to a tropoelastin, or a bioactive fragment thereof (e.g., SEQ ID NO: 2, SEQ ID NO: 3, SEQ ID NO: 4, SEQ ID NO: 5, SEQ ID NO: 6).

Variants of bioactive fragments of tropoelastin comprise an amino acid sequence at least 60%, 70%, 75%, 80%, 83%, 85%, 90%, 95%, 98%, or 99% identical to the corresponding fragment of native tropoelastin. Such bioactive fragments retain one or more of the biological activities of full length tropoelastin.

Additionally, certain bioactive fragments are repeated multiple times within the context of the native tropoelastin protein. For example, the hexameric sequence depicted in SEQ ID NO: 5 is repeated multiple times within the context of the native protein. Accordingly, the invention contemplates compositions and devices comprising or consisting essentially of one or more repeats of a particular bioactive fragment. For example, the invention contemplates compositions comprising or consisting essentially of 1, 2, 3, 4, 5, 6, or 7 repeats of the hexameric sequence represented in SEQ ID NO: 5. Additionally, although the C-terminal fragment in not repeated in the context of the native protein, the invention contemplates compositions comprising or consisting essentially of 1, 2, 3, 4, 5, 6, or 7 repeats of the sequence represented in SEQ ID NO: 6. Note that one of skill in the art can readily make and test compositions comprising multiple repeats of a particular fragment without undue experimentation.

In addition to the polypeptides and fragments described in detail above, the present invention also pertains to isolated nucleic acids comprising nucleotide sequences that encode said polypeptides and fragments. The term nucleic acid as used herein is intended to include fragments as equivalents, wherein such fragments have substantially the same function as the full length nucleic acid sequence from which it is derived. Equivalent nucleotide sequences will include sequences that differ by one or more nucleotide substitutions, additions or deletions, such as allelic variants; and will, therefore, include sequences that differ from the nucleotide sequence of, for example, the wildtype tropoelastin (SEQ ID NO:1). Equivalent sequences include those that vary from a known wildtype or variant sequence due to the degeneracy of the genetic code. Equivalent sequences may also include nucleotide sequences that hybridize under stringent conditions (i.e., equivalent to about 20-27° C. below the melting temperature ($T_m$) of the DNA duplex formed in about 1M salt) to the nucleotide sequence of an elastin-based composition. Further examples of stringent hybridization conditions include a wash step of 0.2×SSC at 65° C.

In one example, the invention contemplates a composition encoded or encodable by a nucleic acid sequence which hybridizes under stringent conditions, including a wash step of 0.2×SSC at 65° C., to a nucleic acid sequence of SEQ ID NO: 1.

Equivalent nucleotide sequences for use in the methods described herein also include sequences which are at least 60% identical to a give nucleotide sequence. In another embodiment, the nucleotide sequence is at least 70%, 75%, 80%, 85%, 90%, 95%, 98%, 99%, or 100% identical to the nucleotide sequence of a native sequence that encodes an elastin-based composition and retains one or more of the biological activities of the native tropoelastin.

Nucleic acids having a sequence that differs from nucleotide sequences which encode a particular elastin-based composition due to degeneracy in the genetic code are also within the scope of the invention. Such nucleic acids encode functionally equivalent peptides but differ in sequence from wildtype sequences known in the art due to degeneracy in the genetic code. For example, a number of amino acids are designated by more than one triplet. Codons that specify the same amino acid, or synonyms (for example, CAU and CAC each encode histidine) may result in "silent" mutations which do not affect the amino acid sequence. However, it is expected that DNA sequence polymorphisms that do lead to changes in the amino acid sequences will also exist One skilled in the art will appreciate that these variations in one or more nucleotides (up to about 3-5% of the nucleotides) of the nucleic acids encoding polypeptides having one or more of the biological activities of native tropoelastin may exist among individuals of a given species due to natural allelic variation.

Peptidomimetics: In other embodiments, the invention contemplates that the composition comprises a peptidomimetic (herein referred to interchangeably as a mimetic of an elastin-based composition). Preferable peptidomimetics retain one or more of the biological activities of native tropoelastin, Peptidomimetics are compounds based on, or derived from, peptides and proteins. The peptidomimetics of the present invention can be obtained by structural modification of the amino acid sequence of a known elastin-based composition using unnatural amino acids, conformational restraints, isosteric replacement, and the like. The subject peptidomimetics constitute the continuum of structural space between peptides and non-peptide synthetic structures.

Exemplary peptidomimetics can have such attributes as being non-hydrolyzable (e.g., increased stability against proteases or other physiological conditions which degrade the corresponding peptide), having increased specificity and/or potency, and having increased cell permeability for intracellular localization. For illustrative purposes, peptide analogs of the present invention can be generated using, for example, benzodiazepines (e.g., see Freidinger et al. in Peptides: Chemistry and Biology, G. R. Marshall ed., ESCOM Publisher: Leiden, Netherlands, 1988), substituted gama lactam rings (Garvey et al. in Peptides: Chemistry and Biology, G. R. Marshall ed., ESCOM Publisher: Leiden, Netherlands, 1988, p 123), C-7 mimics (Huffman et al. in Peptides: Chemistry and Biology, G. R. Marshall ed., ESCOM Publisher: Leiden, Netherlands, 1988, p. 105), keto-methylene pseudopeptides (Ewenson et al. (1986) J Med Chem 29:295; and Ewenson et al. in Peptides, Structure and Function (Proceedings of the 9th American Peptide Symposium) Pierce Chemical Co. Rockland, Ill., 1985), β-turn dipeptide cores (Nagai et al. (1985) Tetrahedron Lett 26:647; and Sato et al. (1986) J Chem Soc Perkin Trans 1:1231), β-aminoalcohols (Gordon et al. (1985) Biochem Biophys Res Commun 126:419; and Dann et al. (1986) Biochem Biophys Res Commun 134:71), diaminoketones (Natarajan et al. (1984) Biochem Biophys Res Commun 124:141), and methyleneamino-modified (Roark et al. in Peptides: Chemistry and Biology, G. R. Marshall ed., ESCOM Publisher: Leiden, Netherlands, 1988, p 134). Also, see generally, Session III: Analytic and synthetic methods, in in Peptides: Chemistry and Biology, G. R. Marshall ed., ESCOM Publisher Leiden, Netherlands, 1988)

In addition to a variety of sidechain replacements which can be carried out to generate the subject peptidomimetics, the present invention specifically contemplates the use of conformationally restrained mimics of peptide secondary structure. Numerous surrogates have been developed for the amide bond of peptides. Frequently exploited surrogates for the amide bond include the following groups (i) trans-olefins, (ii) fluoroalkene, (iii) methyleneamino, (iv) phosphonamides, and (v) sulfonamides.

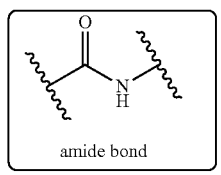 [SMILES: *NC(*)=O]

Examples of Surrogates

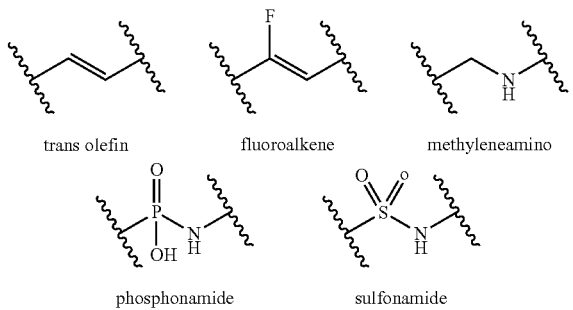

Additionally, peptidomimetics based on more substantial modifications of the backbone of a peptide can be used. Peptidomimetics which fall in this category include (i) retro-inverso analogs, and (ii) N-alkyl glycine analogs (so-called peptoids).

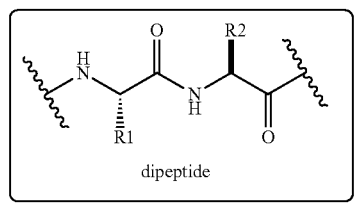

Examples of Analogs

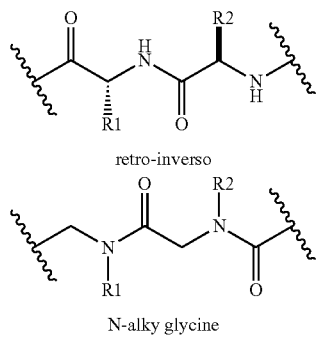

Furthermore, the methods of combinatorial chemistry are being brought to bear, e.g., PCT publication WO 99/48897, on the development of new peptidomimetics. For example, one embodiment of a so-called "peptide morphing" strategy focuses on the random generation of a library of peptide analogs that comprise a wide range of peptide bond substitutes.

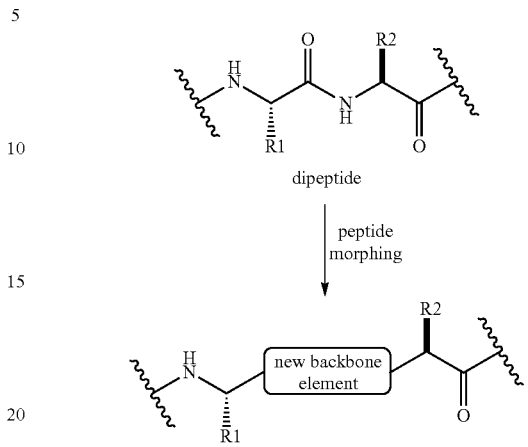

In an exemplary embodiment, the peptidomimetic can be derived as a retro-inverso analog of the peptide. Retro-inverso analogs can be made according to the methods known in the art, such as that described by the Sisto et al. U.S. Pat. No. 4,522,752. As a general guide, sites which are most susceptible to proteolysis are typically altered, with less susceptible amide linkages being optional for mimetic switching The final product, or intermediates thereof, can be purified by HPLC.

In another illustrative embodiment, the peptidomimetic can be derived as a retro-enantio analog of the peptide, such as the exemplary retro-enantio peptide analog derived for the illustrative Val Gly Val Ala Pro Gly peptide (SEQ ID No. 5):

```
                                              (SEQ ID No. 7)
NH2-(d)Gly-(d)Pro-(d)Ala-(d)Val-(d)Gly-(d)Val-
COOH
```

Retro-enantio analogs such as this can be synthesized using commercially available D-amino acids (or analogs thereof) and standard solid- or solution-phase peptide-synthesis techniques. For example, in a preferred solid-phase synthesis method, a suitably amino-protected (t-butyloxycarbonyl, Boc) residue (or analog thereof) is covalently bound to a solid support such as chloromethyl resin. The resin is washed with dichloromethane (DCM), and the BOC protecting group removed by treatment with TFA in DCM. The resin is washed and neutralized, and the next Boc-protected D-amino acid is introduced by coupling with diisopropylcarbodiimide. The resin is again washed, and the cycle repeated for each of the remaining amino acids in turn. When synthesis of the protected retro-enantio peptide is complete, the protecting groups are removed and the peptide cleaved from the solid support by treatment with hydrofluoric acid/anisole/dimethyl sulfide/thioanisole. The final product is purified by HPLC to yield the pure retro-enantio analog.

In still another illustrative embodiment, trans-olefin derivatives can be made for any of the subject polypeptides. A trans olefin analog can be synthesized according to the method of Y. K. Shue et at (1987) *Tetrahedron Letters* 28:3225 and also according to other methods known in the art. It will be appreciated that variations in the cited procedure, or other procedures available, may be necessary according to the nature of the reagent used.

It is further possible to couple the pseudodipeptides synthesized by the above method to other pseudodipeptides, to make peptide analogs with several olefinic functionalities in place of amide functionalities.

Still another classes of peptidomimetic derivatives include phosphonate derivatives. The synthesis of such phosphonate derivatives can be adapted from known synthesis schemes. See, for example, Loots et al. in *Peptides: Chemistry and Biology*, (Escom Science Publishers, Leiden, 1988, p. 118); Petrillo et al. in *Peptides: Structure and Function* (Proceedings of the 9th American Peptide Symposium, Pierce Chemical Co. Rockland, Ill., 1985).

Many other peptidomimetic structures are known in the art and can be readily adapted for use in designing elastin-based composition peptidomimetics. To illustrate, the peptidomimetic may incorporate the 1-azabicyclo[4.3.0]nonane surrogate (see Kim et at (1997) *J. Org. Chem.* 62:2847), or an N-acyl piperazic acid (see Xi et al. (1998) *J. Am. Chem. Soc.* 120:80), or a 2-substituted piperazine moiety as a constrained amino acid analogue (see Williams et al. (1996) *J. Med. Chem.* 39:1345-1348). In still other embodiments, certain amino acid residues can be replaced with aryl and bi-aryl moieties, e.g., monocyclic or bicyclic aromatic or heteroaromatic nucleus, or a biaromatic, aromatic, heteroaromatic, or biheteroaromatic nucleus.

The subject peptidomimetics can be optimized by, e.g., combinatorial synthesis techniques combined with high throughput screening techniques, and furthermore can be tested to ensure that the peptidomimetic retains one or more of the biological activities of native tropoelastin.

The invention contemplates methods, compositions, and devices for promoting adhesion and/or migration of endothelial cells. The invention contemplates the use of a single elastin composition (e.g., a tropoelastin polypeptide; a single bioactive fragment; a single peptidomimetic), as well as the use of more than one elastin composition used concurrently or consecutively. Accordingly, the invention contemplates embodiments in which a tropoelastin polypeptide and one or more tropoelastin fragments or peptidomimetics are used concurrently or consecutively. The invention contemplates embodiments in which two or more tropoelastin fragments or peptidomimetics are used.

The present invention provides methods, compositions, and devices to promote adhesion and/or migration of endothelial cells. Tropoelastin, or one or more bioactive fragments thereof, can be used to promote endothelial adhesion and/or migration. In certain embodiments, tropoelastin, or a bioactive fragment thereof, is covalently appended to a device, and the tropoelastin, or a bioactive fragment thereof, promotes adhesion of endothelial cells to the metal device. The invention contemplates methods of promoting endothelial cell adhesion using any of the following: tropoelastin; a bioactive fragment thereof; a peptidomimetic; more than one bioactive fragment thereof; more than one peptidomimetic; or a combination of full length tropoelastin and one or more bioactive figments or peptidomimetics thereof.

The present invention provides methods, compositions, and devices to promote adhesion and/or migration of endothelial cells. Exemplary endothelial cells include, but are not limited to, endothelial stem cells. The methods, compositions, and devices of the invention can be used in vitro or in vivo. Endothelialization of devices can occur in vivo following device placement. In vivo endothelialization occurs as endogenous endothelial cells adhere to the device. Endothelialization of devices can also occur in vitro prior to device placement. In other words, a device can be pre-seeded with endothelial cells, for example endothelial cells derived from the patient, prior to placement. Further endothelialization may occur following device placement.

The effect of elastin on endothelial cell migration and proliferation offers unique therapeutic advantages to prevent some of the complications that are associated with the placement of intravascular devices, such as coronary stents. Recently deployed coronary stents carry with them increased rates of in situ thrombosis, which rates of thrombosis decrease dramatically once the metal struts of the stent have endothelialized. This necessitates the use of multiple antiplatelet agents, such as aspirin and clopidogrel, until such endothelialization has occurred. While usually tolerated well, such antiplatelet use can cause treatment dilemmas when surgical procedures are required or when the patients have disease such as atrial fibrillation that require other methods of anticoagulation, such as inhibition of vitamin K-dependent coagulation factors. Materials that promote more rapid intravascular endothelialization of intravascular devices would not only reduce in situ rates of thrombosis but also could potentially decrease the necessary time for dual anti-platelet therapy.

Accordingly, the present invention provides methods for reducing thrombosis. The present invention further provides methods for reducing the necessary treatment time for anti-platelet therapy.

An additional complication of coronary stout placement is the subsequent risk of smooth muscle cell hyperproliferation and in stent restenosis, especially in high risk individuals such as those with diabetes. Drug-eluting stent platforms have been developed in an attempt to combat this restenosis. Through the elution of cytoxic agents, drug-eluting stents have largely overcome the problem of restenosis and have extended the reach of interventional cardiology to include high risk lesions that previously would have solidly been within the domain of cardiothoracic surgery. However, drug-eluting stents have also perhaps increased the time frame during which in situ thrombosis may occur, with cases of in stent thrombosis occurring sometimes >1 year after drug-eluting stent (DES) placement. This likely results from delayed endothelialization that occurs with prolonged elution of the cytotoxic agent.

The use of tropoelastin, or bioactive fragments thereof, may provide an opportunity to overcome both of these limitations. Here we demonstrate that elastin promotes endothelial migration. Such enhanced migration may result in more rapid device endothelialization by migration/invasion by the surrounding endothelium. Additionally, we demonstrate that stainless steel surfaces with covalently attached elastin have markedly increased adherence of endothelial cells and endothelial progenitor cells than similar bare metal surfaces. In addition, addition, the adherent endothelial cells have a spread cytoplasm as they might after adhesion to an intact internal elastic lamina. Given the ability of tropoelastin, and bioactive fragments thereof, to promote adhesion and/or migration of endothelial cells, these polypeptides can be used in methods and devices to decrease thrombosis and restenosis. The polypeptides can be used alone or can be used in combination, with other devices or therapies.

In certain embodiments, the invention provides methods for promoting endothelial cell adhesion using a combination of tropoelastin (or a fragment) with one or more other agents that promote adhesion. For example, tropoelastin (or a fragment) can be used concurrently or consecutively with an anti-CD34 antibody. In certain embodiments, the invention provides methods and devices using both an elastin-based composition and anti-CD34 antibody.

Previously we have described the effect of elastin on smooth muscle migration and differentiation and have demonstrated the ability of an elastin sheath to reduce in stent intimal hyperplasia. Stainless steel devices coated with elastin may not only endothelialize rapidly buy may have the added benefit of reduced subsequent intimal hyperplasia.

The foregoing description of intravascular thrombosis following stent placement provides a specific example illustrating a general problem associated with the placement of any device into the body or into a vessel lumen. Thrombosis is a problem associated with placement of stents, catheters, wires, shunts, and other intraluminal devices, regardless of whether the devices are placed intravascularly or into another type of vessel. Furthermore, thrombosis is a problem associated with the placement of larger devices including cardioverter-defibrillators, pacemakers, chest tubes, ventricular-assist devices, ventilators, patent foramen ovale closure devices, and the like. The risk of thrombosis often necessitates antiplatelet or anticoagulant management, and increases the overall risk of these procedures. On a whole, the risks associated with thrombosis greatly influence interventional treatment of a wide range of diseases and conditions including, but not limited to cardiovascular conditions.

In certain embodiments, the amount of tropoelastin, or a bioactive fragment thereof, effective to promote adhesion of endothelial cells is an amount sufficient to promote and maintain adhesion of endothelial cells under physiologically relevant conditions of flow rate and pressure. Such physiologically relevant conditions are the flow rate and pressure conditions encountered in an artery or vein, or fluid flow rate and pressure conditions encountered within another body vessel. The use of amounts of tropoelastin, or a bioactive fragment thereof effective to maintain adhesion under physiological conditions of arterial and/or venous blood flow and pressure, or fluid flow and pressure conditions encountered within another body vessel, is an important step in the effective in vivo use of tropoelastin compositions and devices appended with tropoelastin compositions.

In certain embodiments, the amount of tropoelastin or a bioactive fragment used to promote adhesion and/or migration is an amount effective to promote and maintain adhesion of endothelial cells under physiologically relevant conditions. For example, the amount of tropoelastin or a bioactive fragment covalently attached to a device comprises an amount effective to promote and maintain adhesion of endothelial cells under physiologically relevant conditions. Exemplary effective amounts are at least about 100 ng/square centimeter, at least about 150 ng/square centimeter, or least about 200 ng/square centimeter of device surface. Further exemplary effective amounts are at least about 250 ng/square centimeter, at least about 275 ng/square centimeter, or at least about 300 ng/square centimeter. Still additional exemplary effective amounts are at least about 310 ng/square centimeter, at least about 325 ng/square centimeter, at least about 350 ng/square centimeter, at least about 375 ng/square centimeter, or at least about 400 ng/square centimeter. Still additional exemplary effective amounts are at least about 450 ng/square centimeter, at least about 500 ng/square centimeter, at least about 550 ng/square centimeter, at least about 600 ng/square centimeter, at least about 625 ng/square centimeter, or at least about 650 ng/square centimeter, or at least about 700 ng/square centimeter. The invention recognizes and contemplates that the amount effective to promote and maintain adhesion under physiologically relevant conditions may vary depending on the particular vessel into which the device is placed, as well as the underlying disease state or physiology of the patient. Furthermore, the effective amount may vary depending on the device material, as some materials are more thrombogenic than other materials. For example, metal is particularly thrombogenic, and the risk of thrombosis following placement of a metal device is greater than the risk of thrombosis following placement of devices made from other materials. One of skill in the art can determine the optimal conditions for treating a particular patient.

Exemplary devices may be made from or coated with any of a number of materials. As detailed throughout, the invention contemplates attaching tropoelastin or bioactive fragments thereof to virtually any device that, in use, is placed into a vessel in a human or animal body. Exemplary materials are biocompatible materials typically used in the manufacture of medical devices. By way of examples, devices may be made from or coated with metal, plastic, silicone, dacron, PTFE, or derivatives or alloys thereof. The subject polypeptides can be covalently attached to or crosslinked to the device surface. Methods of covalently attaching polypeptides to solid surfaces are well known in the art. One example is provided herein. However, other methods of attaching polypeptides to surfaces known in the art are similarly contemplated and can be readily used. One of skill in the art can select amongst various attachment chemistries and methods depending on the concentration of protein to be attached and the nature of the device surface to which attachment is desired.

(v) Method of Screening

This application describes methods and compositions for promoting adhesion and migration of endothelial cells and endothelial progenitor cells using compositions comprising tropoelastin, or bioactive fragments thereof. With the importance of providing effective devices, methods, and compositions for preventing and/or decreasing restenosis and thrombosis, the present invention recognizes the utility in screening to identify tropoelastin variant polypeptides, bioactive fragments of tropoelastin, as well as peptidomimetics that might be useful in promoting adhesion and/or migration of endothelial cells. Exemplary fragments, variants, and peptidomimetics identified and/or characterized by the methods of the present invention retain one or more of the following biological activities of native tropoelastin: (i) promotes adhesion of endothelial cells in vitro; (ii) promotes adhesion of endothelial cells in vivo; (iii) promotes adhesion of human aortic endothelial cells (HuAEC) in vitro; (iv) promotes adhesion of human aortic smooth muscle cells (HuAoSMC) in vitro; (v) promotes migration of endothelial cells in vitro; (vi) promotes migration of human aortic endothelial cells (HuAEC) in vitro; (vii) promotes adhesion of A2058 human melanoma cells in vitro; (viii) promotes migration, of A2058 human melanoma cells in vitro; (ix) promotes adhesion of human microvessel endothelial cells (HMVEC) in vitro. Variants, fragments, and peptidomimetics identified by the screening methods of the invention can then be further analyzed to determine whether they are useful in vivo for treating or preventing restenosis and/or thrombosis.

The screening methods contemplated include screening single candidate polypeptides, as well as libraries of polypeptides. Furthermore, the screening methods can be conducted as high throughput assays.

In the context of the present invention, a cell based screen can be conducted in endothelial cells or endothelial cell lines in culture. Exemplary endothelial cells or cell lines can be derived from any species including, but not limited to, humans, mice, rats, rabbits, cows, pigs, non-human primates, and the like. Furthermore, exemplary endothelial cells include endothelial progenitor cells or transformed endothelial cell lines. By way of non-limiting example, the screen can be conducted in cultures of human aortic endothelial cells (HuAECs) or human microvessel endothelial cells (HMVECs).

Regardless of the particular cell type used, cultures of the cells can be contacted with one or more candidate polypeptides and assayed for cell adhesion and/or cell migration. As a control, the effect of the candidate polypeptide can be compared to behavior of the cells in the absence of polypeptide or in the presence of a carrier such as BSA. Using this method, potentially useful polypeptide variants, fragments, or peptidomimetics can be identified and/or characterized. Specifically, polypeptides that promote adhesion and/or migration of endothelial cells in comparison to the behavior of the cells in the absence of polypeptide or in the presence of carrier only, are polypeptides that may be useful in the methods of the present invention. Such polypeptides can be further analyzed using additional in vitro or in vivo assays.

Regardless of the methodology used to identify and/or characterize a tropoelastin polypeptide variant, fragment, or peptidomimetic, polypeptides identified as promoting endothelial adhesion and/or migration in vitro have a variety of in vitro or in vivo uses. Accordingly, the invention further contemplates the use of a polypeptide identified by the screening methods of the invention. Identified elastin-based compositions may be used alone or in combination with other agents, or may be formulated in a pharmaceutically acceptable carrier.

The invention also contemplates various methods for testing the efficacy of various devices to which tropoelastin or peptide fragments have been attached. For example, devices made of various materials (e.g., plastic, metal, PTFE, silicone) can be coated with an effective amount of tropoelastin or bioactive fragment via crosslinking or via a covalent linkage. Coated devices can be inserted into the vessel of an animal model. For example, pigs are often used as an animal model for cardiovascular indications. Coated devices can be placed into an artery or vein of a pig. The thrombogenic effect of the implanted device can be compared to the thrombogenic effect of a bare metal device placed into the artery or vein of a control animal. Given that metal is typically the most thrombogenic of device materials, the use of a bare metal control represents the maximal level of device thrombosis.

Imaging can be used to view the implanted device. At some point following the experiment, the device can be removed and imaged to assess the relative endothelialization of the various coated devices in comparison to the bare metal device.

Similar experiments can be conducted using other vessels and other animal models. Furthermore, experiments can be conducted using injured or diseased animals. Given that medical devices are implanted in sick or injured patients, the use of sick animals may provide a more accurate model of the thrombogenic process.

(v) Methods of Administration of Nucleic Acids, Proteins, Chemical Compounds and Pharmaceutical Compositions of Agents The invention further contemplates pharmaceutical compositions including tropoelastin polypeptide, and bioactive fragments thereof. The pharmaceutical compositions comprise a tropoelastin polypeptide, and bioactive fragments thereof formulated, in one embodiment, according to conventional pharmaceutical compounding techniques. See, for example, Remington's Pharmaceutical Sciences, 18th Ed. (1990, Mack Publishing Co., Easton, Pa.). Pharmaceutical formulations of the invention can contain the active agent or a pharmaceutically acceptable salt of the active agent. These compositions can include, in addition to an active agent, a pharmaceutically acceptable excipient, carrier, buffer, stabilizer or other material well known in the art. Such materials should be non-toxic and should not interfere with the efficacy of the active agent. Preferable pharmaceutical compositions are non-pyrogenic. Additional preferred pharmaceutical compositions are non-antigenic. The carrier may take a wide variety of forms depending on the route of administration, e.g., intravenous, intravascular, oral, intrathecal, epineural or parenteral, transdermal, pulmonary, etc. Additionally, the carrier is appropriate for covalent attachment of the tropoelastin polypeptide, or bioactive fragment thereof, to a metal device.

Illustrative examples of suitable carriers are water, saline, dextrose solutions, fructose solutions, ethanol, or oils of animal, vegetative or synthetic origin. The carrier may also contain other ingredients, for example, preservatives, suspending agents, solubilizing agents, buffers and the like.

Pharmaceutical compositions according to the invention include devices. Such devices are covalently conjugated with a composition comprising tropoelastin, or a bioactive fragment thereof. Tropoelastin compositions can also be cross-inked to a device surface. Coated devices are appropriate for administration (e.g., insertion, implantation, delivery) into a human or animal body. Coated devices have optionally been approved by the FDA for one or more indications.

Exemplary devices are metal devices of virtually any shape or size appropriate for the particular indication. Exemplary metals can be chosen by one of skill in the art but include, without limitation stainless steel, surgical steel, titanium, gold, silver, platinum, nitinol, aluminum, nickel, and other metals and metal alloys appropriate for implantation into a human or animal body. Further exemplary devices are made of or coated with plastic, silicone, Dacron, PTFE, or derivatives or combinations thereof.

Exemplary devices include, without limitation, stents, catheters, wires, and other intraluminal devices. Further exemplary devices include shunts, chest tubes, patent foramen ovale closure devices, cardioverter-defibrillators, pacemakers, endovascular grafts, mechanical hearts, mechanical heart valves, ventricular-assist devices, and ventilators. Such devices can be delivered intravenously, intravascularly, intraarterially, orally, rectally, surgically, urethrally, or by other methods known in the art for appropriately delivering a particular device.

One of skill in the art will readily recognize that thrombosis and restenosis are issues faced not only in association with the treatment of cardiovascular diseases, but also in other occlusive body vessel diseases and disorders. Furthermore, thrombosis is a potential issue associated with the implantation of any medical device regardless of the particular indication for which the medical device constitutes a treatment. Accordingly, the invention contemplates methods and devices for use in a variety of body vessels and in association with a variety of disease indications. By way of example, exemplary body vessels include, but are not limited to, artery, vein, common bile duct, pancreatic duct, kidney duct, esophagus, trachea, urethra, bladder, uterus, ovarian duct, Fallopian tube, vas deferens, prostatic duct, or lymphatic duct. Further specific devices appropriate for non-cardiovascular indications include, but are not limited to, gallbladder stents, endrotracheal stents, bladder drainage catheters, cerebral-peritoneal shunt catheters, dialysis catheters, grafts or catheters for peritoneal dialysis, and the like. In short, the invention is based on the recognition and appreciation that virtually every medical intervention that involves the placing of a device, temporarily or permanently, into a human or animal body creates a risk of thrombosis. Accordingly, the present invention provides methods and compositions that can be used as part of virtually any such medical intervention to reduce the risk of thrombosis.

The invention also provides articles of manufacture including pharmaceutical compositions of the invention, devices, and related kits. The invention encompasses any type of article including a pharmaceutical composition of the invention, but the article of manufacture is typically a container, preferably bearing a label identifying the composition contained therein, as well as instructions for use of the composition and/or device.

In another embodiment of any of the foregoing, the invention contemplates that a device coated with tropoelastin, or bioactive fragment thereof, can further be pre-coated (coated prior to implantation into a human or non-human patient) with endothelial cells. In such embodiments, endothelial cells or endothelial progenitor cells (e.g., either harvested from the same patient or from a related or unrelated donor) would be adhered to the tropoelastin-coated devices ex vivo. These devices would then be implanted into the patient. Without being bound by theory, once implanted into the body, the patient's own cells may additionally adhere to the device. However, regardless of whether further endothelial adhesion occurred in vivo, the device would already be coated with endothelial cells or endothelial progenitor cells, thereby decreasing or preventing restenosis or thrombosis.

One of skill in the art will recognize that ex vivo seeding of the device with endothelial cells derived from a source other than the same patient could provoke an immune response upon implantation. Accordingly, in one embodiment, the invention contemplates co-administering anti-rejection drugs.

The invention includes a method for prophylaxis or treatment of restenosis or thrombosis associated with the treatment of any cardiovascular or other disorder that requires implantation of a medical device. Exemplary disorders include cardiovascular diseases, obstructive vascular diseases, and the like. By way of example, the invention contemplates methods for the prophylaxis or treatment of restenosis or thrombosis following treatment for atherosclerosis, restenosis, vascular bypass graft stenosis, transplant arteriopathy, aneurysm, and dissection. Furthermore, the invention contemplates methods for the prophylaxis or treatment of restenosis or thrombosis following treatment of vessels selected from common bile duct, pancreatic duct, esophagus, trachea, urethra, bladder, uterus, ovarian duct, Fallopian tube, vas deferens, prostatic duct, tear duct, and lymphatic duct. Additionally, the invention recognizes that patients often require device placement as part of the treatment for any of a wide range of diseases and conditions. By way of example, patients suffering from virtually any disease, injury, or condition may need to be placed on a ventilator. In the cases of some patients, placement on a ventilator may be a long term part of treatment. For example, patients with ALS or severe spinal cord injuries, especially those occurring at a high level of the spinal cord, may require long term maintenance on a ventilator. By way of further example, patients on dialysis may require long term use of a peritoneal catheter. The invention contemplates methods, compositions, and devices for decreasing or pr venting thrombosis occurring following device placement associated with the treatment of any disease, condition, or injury.

Regardless of whether the compositions of the invention are used in vitro or in vivo, and regardless of whether they are covalently attached to a device, the invention contemplates that the compositions of the invention can be conveniently formulated for administration with a biologically acceptable medium, such as water, buffered saline, polyol (for example, glycerol, propylene glycol, liquid polyethylene glycol and the like) or suitable mixtures thereof.

Optimal concentrations of the active ingredient(s) in the chosen medium can be determined empirically, according to procedures well known to medicinal chemists. As used herein, "biologically acceptable medium" includes solvents, dispersion media, and the like which may be appropriate for the desired route of administration of the one or more agents. The use of media for pharmaceutically active substances is known in the art. Except insofar as a conventional media or agent is incompatible with the activity of a particular agent or combination of agents, its use in the pharmaceutical preparation of the invention is contemplated. Suitable vehicles and their formulation inclusive of other proteins are described, for example, in the book *Remington's Pharmaceutical Sciences* (Remington's Pharmaceutical Sciences. Mack Publishing Company, Easton, Pa., USA 1985). These vehicles include injectable "deposit formulations".

Methods of introduction may also be provided by delivery via a biocompatible, device. Biocompatible devices suitable for delivery of the subject agents include intraluminal devices such as stents, wires, catheters, sheaths, and the like. However, administration is not limited to delivery via a biocompatible device. As detailed herein, the present invention contemplates any of number of routes of administration and methods of delivery.

The effective amount or dosage level will depend upon a variety of factors including the activity of the particular one or more agents employed, the route of administration, the time of administration, the rate of excretion of the particular agents being employed, the duration of the treatment, other drugs, compounds and/or materials used in combination with the particular agents employed, the age, sex, weight, condition, general health and prior medical history of the animal, and like factors well known in the medical arts.

Agents can be administered alone, or can be administered as a pharmaceutical formulation (composition). Said agents may be formulated for administration in any convenient way for use in human or veterinary medicine. In certain embodiments, the agents included in the pharmaceutical preparation may be active themselves, or may be a prodrug, e.g., capable of being converted to an active compound in a physiological setting.

These compositions may also contain adjuvants such as preservatives, wetting agents, emulsifying agents and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

Exemplification

The invention now being generally described, it will be more readily understood by reference to the following examples which are included merely for purposes of illustration of certain aspects and embodiments of the present invention, and are not intended to limit the invention.

Example 1

Tropoelastin Promotes Adhesion of Endothelial Cells

FIG. 1 shows the effect of fibronectin and tropoelastin on the adhesion of CHO cells, human embryonic kidney cells (HEK 293), human aortic smooth muscle cells (HuAoSMC), and human aortic endothelial cells (HuAEC). Cells were plated on culture plates coated with either 0.1% BSA (as a control), 10 ug/ml fibronectin (FN), or 10 ug/ml recombinant tropoelastin, and assayed for adherence to the coated substrate.

All four of the cell types examined adhered to fibronectin. In contrast, the HuAECs and, to a less extent, the HuAoSMCs, adhered to tropoelastin. However, neither CHO cells nor HEK 293 cells adhered to tropoelastin. These results demonstrated that endothelial cells and smooth muscle cells adhere to tropoelastin. However, unlike the binding of cells to fibronectin, there is some cell-type specificity to the binding of cells to tropoelastin. For example, FIG. 1 shows that CHO cells and HEK 293 cells, which do adhere to fibronectin, do not adhere to tropoelastin. Note that the full length, recombinant tropoelastin used throughout these experiments is represented in SEQ ID NO: 4. Specifically, these experiments were conducted with recombinant human tropoelastin lacking a native signal sequence. Furthermore the protein was engineered to have a 10× His tag on the N-terminus followed by a Factor Xa cleavage site. The total length of the human tropoelastin protein used in these experiments was 706 amino acid residues.

Figure 2:
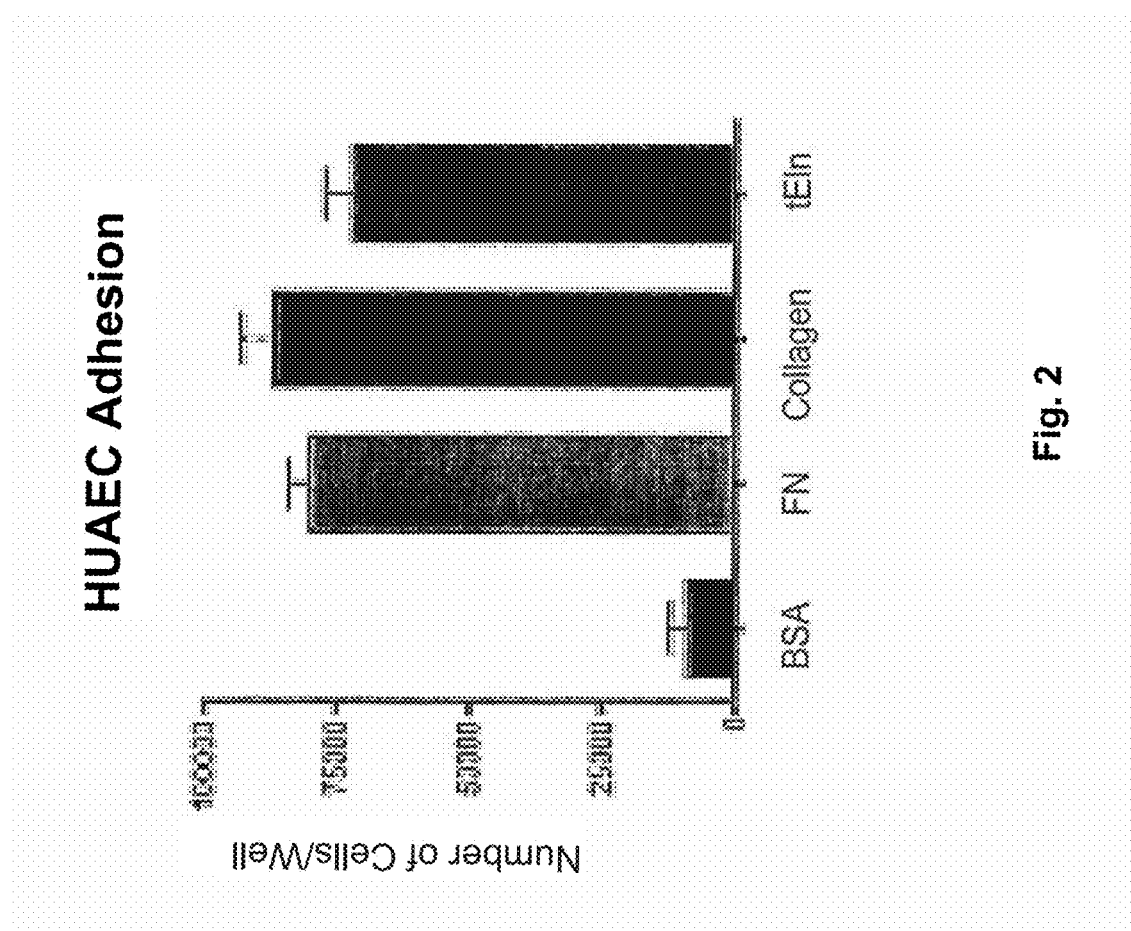
FIG. 2 graphically summarizes the adhesion of endothelial cells to culture dishes coated with a variety of proteins. The adherence of HuAECs to tropoelastin is similar to that observed with fibronectin and collagen.

The results shown in FIG. 1 are depicted graphically in FIG. 2. FIG. 2 shows that tropoelastin promotes adhesion of HuAECs. This cell adhesion, as measured by the number of cells bound/well, is comparable to that observed with fibronectin or collagen.

To determine whether individual combinations of integrins were involved in cell adhesion to wells coated with fibronectin, collagen, or tropoelastin, endothelial cells were incubated with either 25 μg/ml immunoglobulin (IgG, control) or with 25 μg/ml anti-$\alpha_v\beta_3$ or anti-$\alpha_2\beta_1$ blocking antibodies prior to exposing the cells to the coated surfaces. Preincubation with the anti-$\alpha_v\beta_3$ or anti-$\alpha_2\beta_1$ antibodies did not significantly decrease endothelial cell adhesion to surfaces coated with fibronectin or collagen. However, endothelial adhesion to wells coated with tropoelastin was blocked by more than 50% by incubation of the cells with anti-$\alpha_v\beta_3$ blocking antibodies. This suggested that binding of tropoelastin to the integrin $\alpha^v\beta_3$ is an important contributor to endothelial adhesion to tropoelastin-coated surfaces.

Example 2

Figure 3:
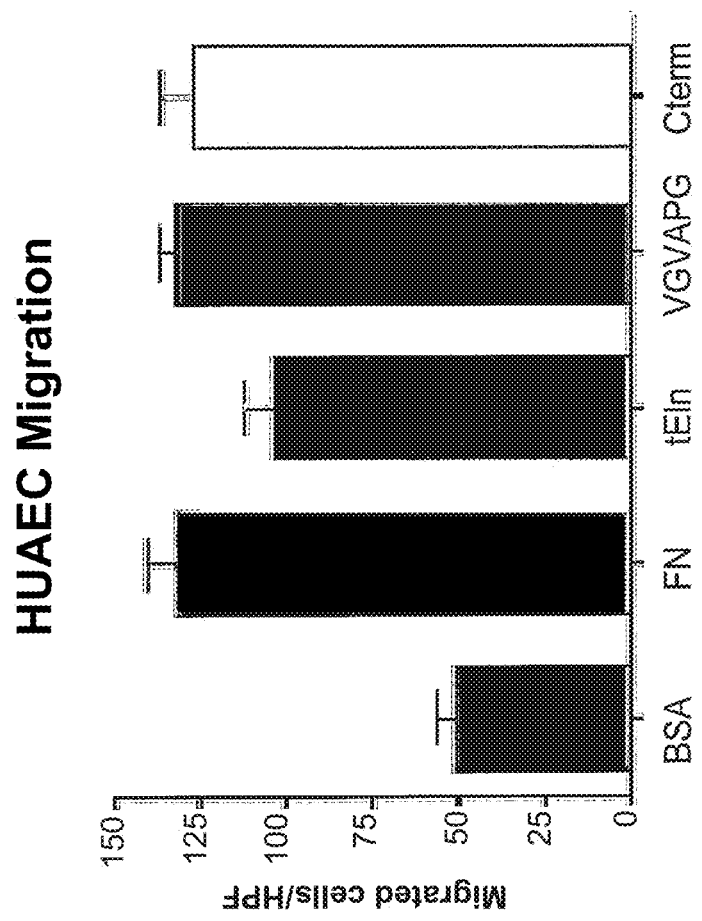
FIG. 3 depicts the effect of tropoelastin, or various bioactive fragments of tropoelastin, on endothelial cell migration. Tropoelastin, as well as two different bioactive fragments of tropoelastin, promote migration of endothelial cells. The effect on endothelial cell migration of tropoelastin, and various bioactive fragments, is comparable to the effect of fibronectin on endothelial cell migration.

Tropoelastin, and Bioactive Fragments Thereof, Promote Migration of Endothelial Cells FIG. 3 graphically summarizes resulting demonstrating that tropoelastin promoted migration of endothelial cells. Migration of HuAECs to BSA, fibronectin, and recombinant tropoelastin was measured. Recombinant tropoelastin promoted endothelial cell migration. Furthermore, tropoelastin promoted cell migration at a level comparable to that of fibronectin.

We additionally evaluated the ability of two bioactive fragments of tropoelastin to promote endothelial cell migration, and these results are also summarized in FIG. 3. We assayed the hexamer VGVAPG (SEQ ID No. 5). This hexameric sequence is repeated multiple times within the full length tropoelastin protein. Furthermore, a single repeat of the hexamer, as well as multiple repeats of the hexamer, have been shown to retain at least some of the biological activities of the full length tropoelastin protein. We additionally assayed a 17 residue C-terminal fragment of the tropoelastin protein. This 17 amino acid residue is depicted in SEQ ID NO: 6 (IFPGGACLGKACGRKRK).

As summarized in FIG. 3, both the hexameric sequence and the C-terminal 17 amino acid residue fragment promoted migration of endothelial cells. The fragments functioned equally well in this assay. Furthermore, the fragments promoted endothelial cell migration at least as well as, and possibly better than, the fall length tropoelastin protein.

FIG. 3: Tropoelastin, and Bioactive Fragments Thereof Promote Adhesion and Migration of A2058 Human Melanoma Cells.

Figure 4:
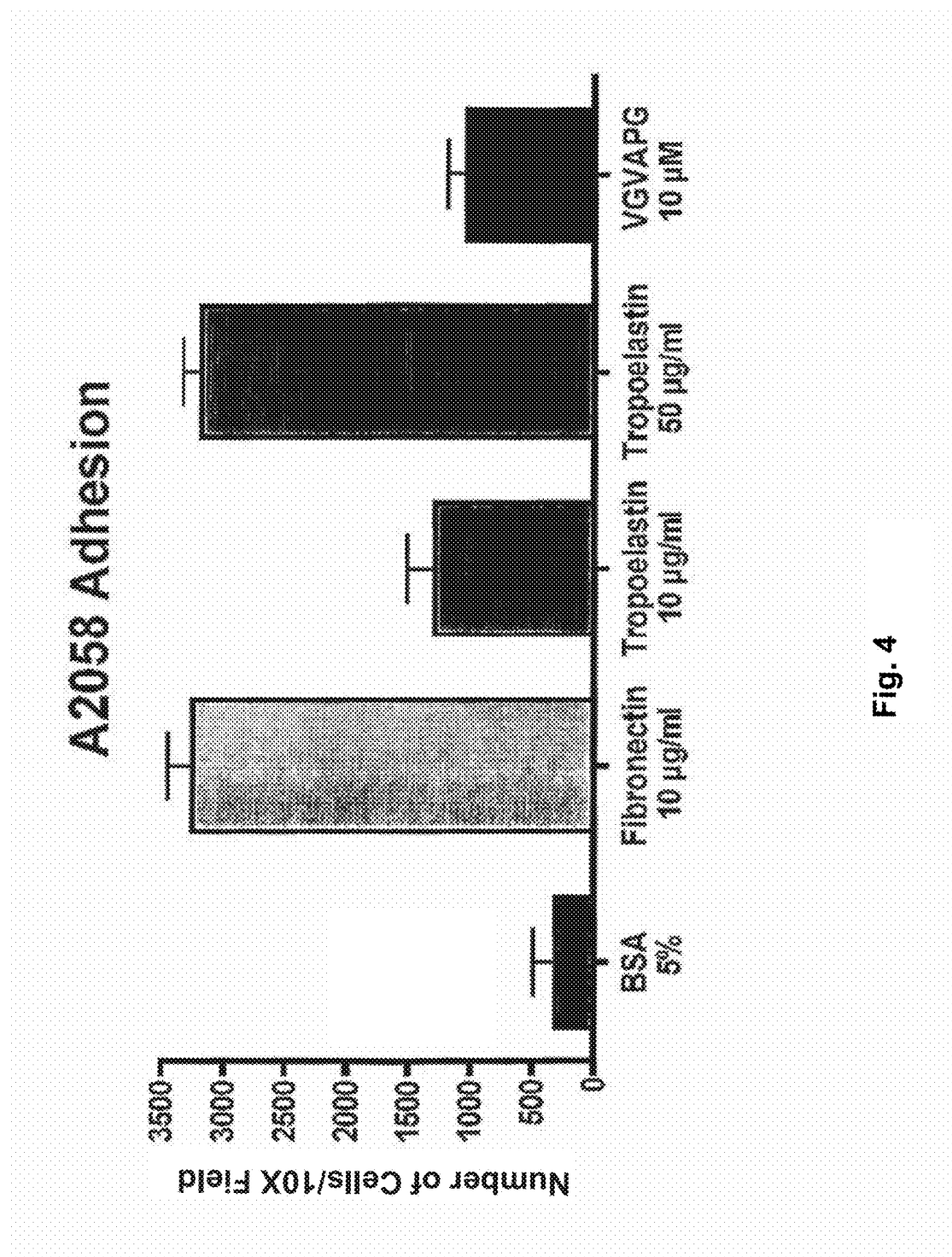
FIG. 4 shows that tropoelastin, and a bioactive fragment of tropoelastin, promote adhesion of A2058 human melanoma cells.

FIG. 4 shows the effect of fibronectin, tropoelastin, and a bioactive fragment of tropoelastin on the adhesion of A2058 human melanoma cells. A2058 cells were assayed for adherence to substrates coated with BSA (control), fibronectin, tropoelastin, or a bioactive fragment of tropoelastin corresponding to a single repeat of the hexameric sequence VGVAPG (SEQ ID No. 5). In comparison to adherence to BSA, A2058 cells adhered to substrates coated with fibronectin tropoelastin, or a bioactive fragment of tropoelastin. Specifically, adhesion to tropoelastin was dose dependent, and cells adhered to 50 μg/ml of tropoelastin similarly to 10 ug/ml of fibronectin. In addition, 10 μM of a single repeat of the hexameric sequence VGVAPG (SEQ ID No. 5) (e.g., a bioactive fragment tropoelastin) promoted adhesion of A2058 cells, in comparison to BSA, and at a level similar to 10 μg/ml of full length tropoelastin.

Figure 5:
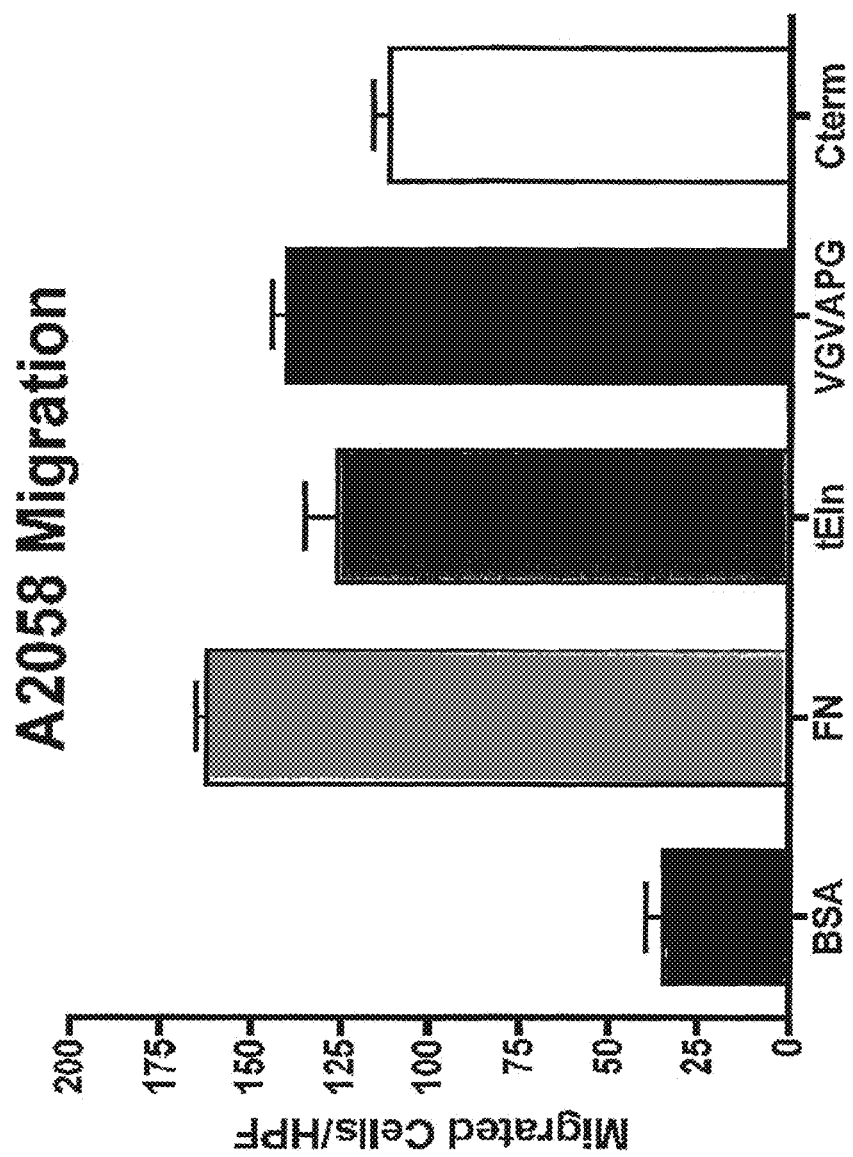
FIG. 5 shows that tropoelastin, and various bioactive fragments of tropoelastin, promote migration of A2058 human melanoma cells.

FIG. 5 shows the effect of fibronectin, tropoelastin, and two different bioactive fragments of tropoelastin on the migration of A2058 human melanoma cells. A2058 cells migrated in response to fibronectin, tropoelastin, a single repeat of hexameric sequence VGVAPG (SEQ ID No. 5) (e.g., a bioactive fragment of tropoelastin), and a C-terminal fragment of tropoelastin (the C-terminal fragment represented in SEQ ID NO: 6). Full length tropoelastin, a single repeat of VGVAPG (SEQ ID No. 5), and the C-terminal fragment represented in SEQ ID NO: 6 all promoted migration of A2058 cell at comparable levels.

Example 4

Endothelial Cells Adhere to Coated Stainless Steel Devices

The present invention is based on the finding that tropoelastin, and bioactive fragments thereof, promote adhesion and migration of endothelial cells. This finding allows the design of methods and compositions to promote adhesion of endothelial cells to devices that are or can be implanted into human or non-human animals. As outlined in detail throughout the application, the coating of devices with endothelial cells (e.g., either prior to placement in the body or in vivo) helps prevent restenosis and thrombosis.

Given that an important aspect of the present invention is the prevention of restenosis and thrombosis, we conducted experiments to address whether endothelial cells would adhere to metal devices that had been coated with tropoelastin. Briefly, tropoelastin was covalently conjugated to a stainless steel disk approximately 6 mm in diameter. Tropoelastin was linked to the disk surface using an intermediate polysaccharide molecule. An exemplary process for covalently linking tropoelastin to the disk surface, and the process used here, is used in the manufacture of Genous Bio-Engineered R Stents. These disks provided ample surface area for microscopic imaging. Disks were also similarly coated with anti-CD34 antibody and with polysaccharide vehicle alone. Stents coated with anti-CD34 antibody using a similar process (Genous Bio-Engineered R Stents) are currently in human clinical trials and have promise to promote capture of circulating endothelial cells and endothelial progenitor cells and to accelerate endothelialization.

Figure 6:
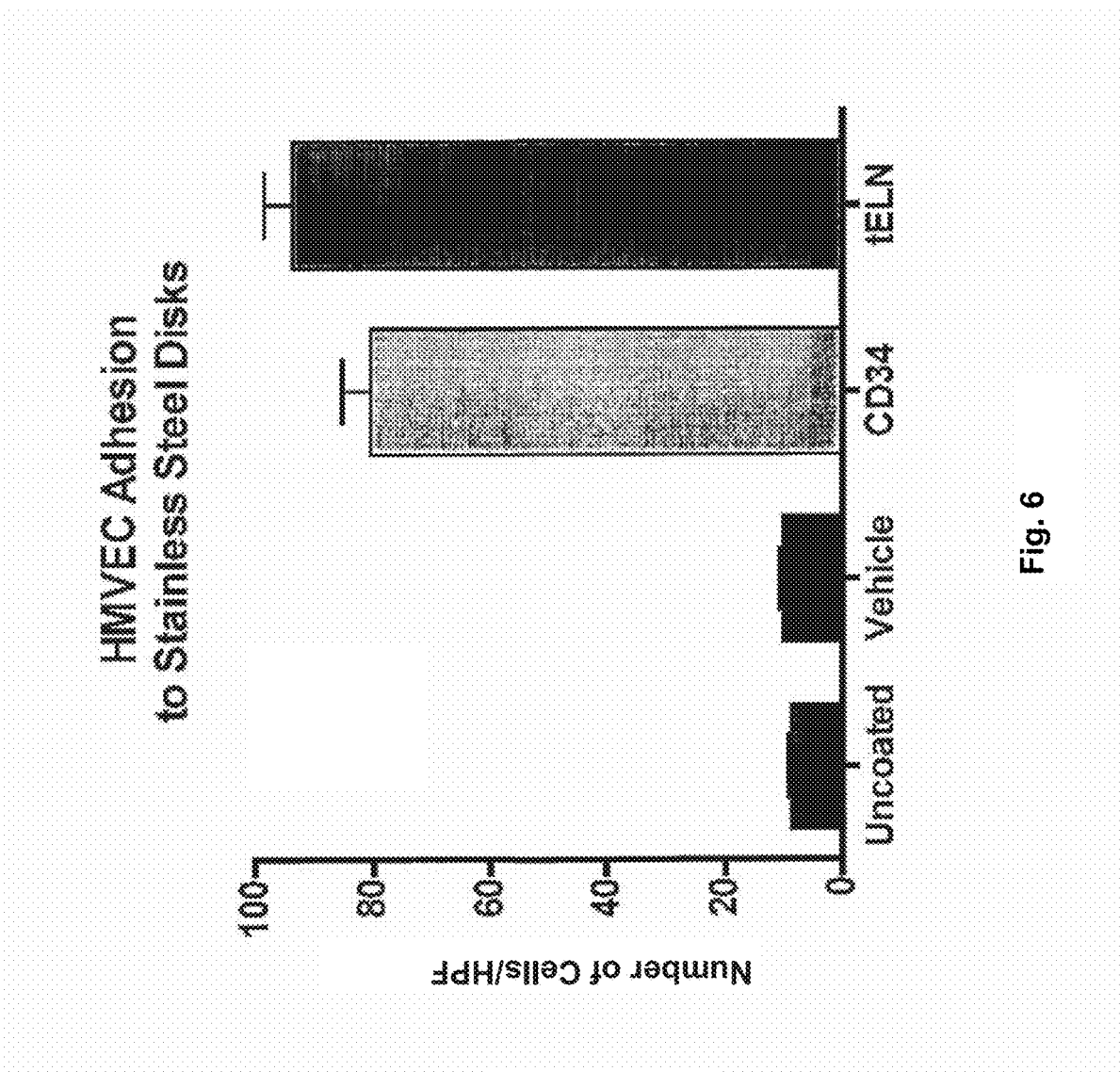
FIG. 6 shows that another human endothelial cell type (human microvessel endothelial cells—HMVEC) adhered to stainless steel disks to which tropoelastin was covalently attached. Adhesion of the HMVECs to the tropoelastin coated stainless steel disks was comparable to the adhesion of HMVECs to stainless steel disks coated with an anti-CD34 antibody.

Human microvessel endothelial cells (HMVEC) were cultured with these coated disks, and adhesion of the cells to the coated disks was assayed. The results of these experiments are summarized in FIG. 6. Tropoelastin promoted adhesion of human endothelial cells to a metal device.

Example 5

Endothelial Cells Adhere to and Spread Across the Surface of Coated Stainless Steel Devices To prevent or treat thrombosis and restenosis, the present invention provides methods and devices for promoting adhesion and/or migration of endothelial cells. In one embodiment, endothelial cells bind to an implantable medical device, thereby decreasing or preventing thrombosis or restenosis. The invention contemplates that the device could be coated with endothelial cells (e.g., either a patient's own endothelial cells or endothelial cells derived from another person or from an animal). Alternatively, the invention contemplates that, following implantation of the device into a patient, the patient's own endothelial cells (e.g., endothelial cells or endothelial progenitor cells) would adhere to the implanted device. Without being bound by theory, the cells could coat the device, in whole or in part, thereby helping to prevent or decrease thrombosis and/or restenosis.

Figure 7:
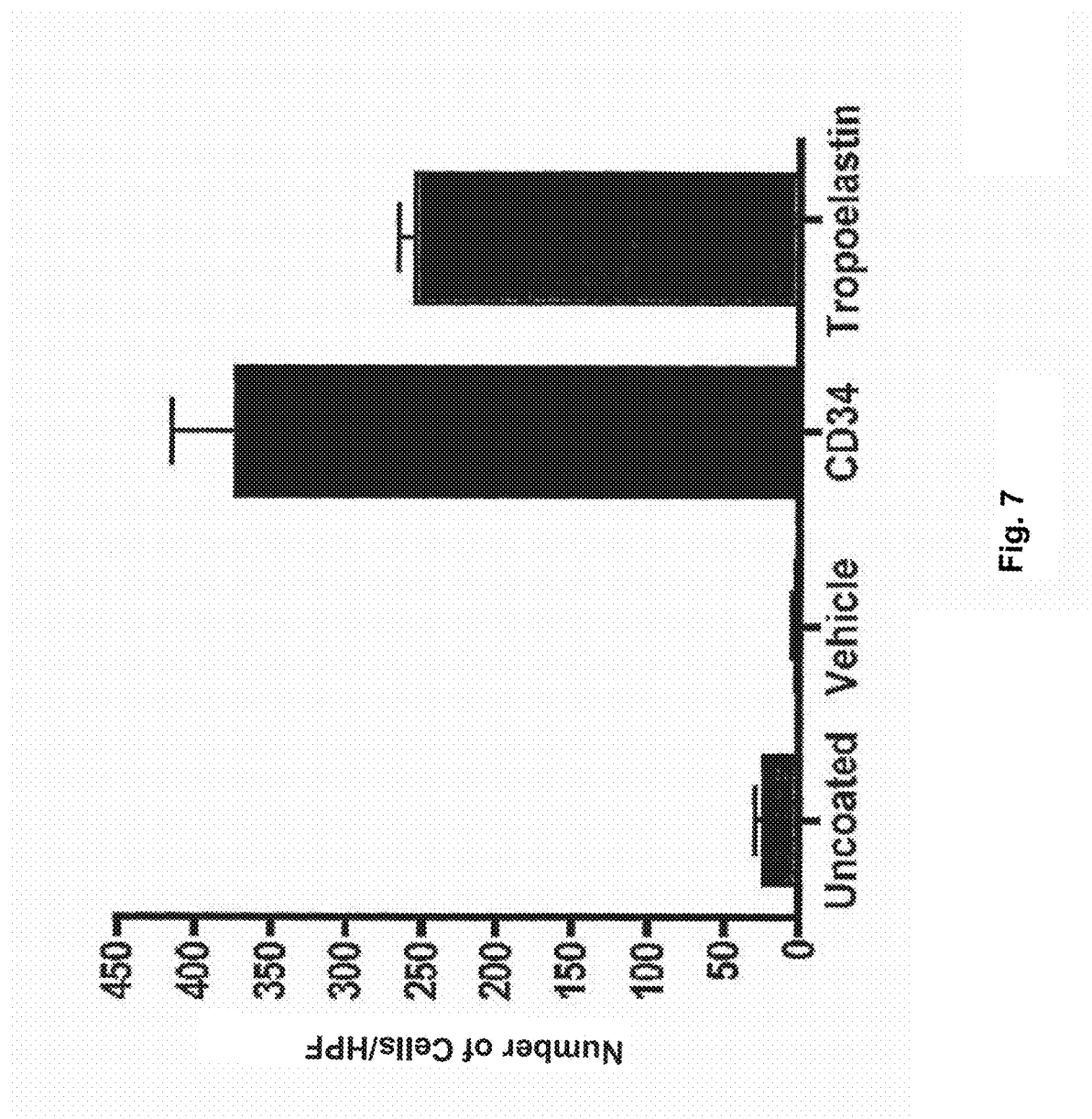
FIG. 7 shows that endothelial progenitor cells adhere to stainless steel disks that have been coated with either an anti-CD34 antibody or with tropoelastin. However, examination of the cells following their binding to the stainless steel disks indicated that adhesion to tropoelastin is associated with cell spreading across the surface of the disk. In contrast, we observed adhesion but not cell spreading of endothelial cells cultured with stainless steel disks coated with an anti-CD34 antibody.

We conducted experiments to assess whether tropoelastin promoted the adhesion of endothelial progenitor cells. Tropoelastin was covalently conjugated to a stainless steel disk approximately 6 mm in diameter. As a control, anti-CD34 antibody (known to promote endothelial cell adhesion) was covalently conjugated to similar stainless steel disks. Endothelial progenitor cells were cultured with these coated disks, and adhesion of the cells to the coated disks was assayed. The results of these experiments are summarized in FIG. 7. Tropoelastin promoted adhesion of human endothelial cells to the metal device.

We also examined the appearance of the adherent endothelial cells. We observed that tropoelastin not only promoted adhesion of the coils to the metal device, but furthermore, promoted spreading of the adherent cells across the surface of the device. This cell spreading was unique to the device coated with tropoelastin and was not observed with the device coated with an anti-CD34 antibody.

Cell spreading was examined by permeabilizing the endothelial cells that had adhered to the coated metal surfaces with Triton X-100 and staining with phalloidin to highlight the actin cytoskeleton and DAPI to mark cell nuclei. As noted above, metal disks coated with either anti-CD34 antibody or with tropoelastin resulted in a significant increase in cell adhesion compared to polysaccharide-coated control disks or to bare metal disks. Endothelial cells adherent to tropoelastin-coated disks had well spread cytoplasm and an organized actin cytoskeleton. Thus, stainless steel surfaces coated with either tropoelastin or anti-CD34 antibody would likely endothelialize more rapidly than would similar bare metal surfaces when intravascularly placed.

The invention contemplates use of metal devices coated with tropoelastin, or a bioactive fragment thereof, to promote adhesion of endothelial cells to the metal device. The invention, also contemplates the use of metal devices coated with both tropoelastin, or a bioactive fragment thereof, and with anti-CD34 antibody. Given the ability of both agents to promote adhesion of endothelial cells, the use of co-coated devices may be advantageous in some instances.

The foregoing experiments used the following methods:

Cell Adhesion Assays 96-well plates were coated in duplicate overnight at 4° C. with 10 µg/ml collagen, fibronectin, tropoelastin, or 0.1% bovine serum albumin (BSA). Cells were harvested with 0.25% trypsin/1 mM EDTA, washed three times in adhesion buffer (0.5% BSA in basal medium), suspended at a working density of $5 \times 10^5$/ml in adhesion buffer, and then allowed to recover for 1 h at 37° C. (5% $CO_2$). For integrin-blocking assays, 25 µg/ml anti-integrin antibodies (Chemicon, Temecula, Calif.) or control IgG (Jackson ImmunoResearch Laboratories, Inc, West Grove, Pa.) were added to the cell suspension during the recovery period. During the cell recovery, the coated 96-well plates were washed twice in dPBS and blocked for 1 h at 25° C. in 5.0% BSA (dPBS). The blocking solution was removed, and the wells were washed twice in dPBS. Recovered cells were added to the coated wells in a volume of 100 µl per well and placed at 37° C. for 30 minutes (5% $CO_2$). Following this incubation, the assay plate was inverted and assay wells were washed twice with 100 µl dPBS to remove non-specifically adhered cells. The wells were then fixed in Zamboni fixative, stained with Gill 1 hematoxylin, and overlayed with 80% glycerol. The assay was imaged at 100× magnification, capturing 3 random fields/well on a Zeiss Axiovert 200 inverted microscope equipped with a Zeiss Axiocam digital camera. Readings represent the number of adherent cells/well (average six high powered 100× fields, three taken from each of two separate wells).

Adhesion Assays on Stainless Steel Disks

Adhesion assays on 6 mm stainless steel disks (Orbus Medical Technologies, Ft Lauderdale, Fla.) pre-coated with anti-CD34 antibody, tropoelastin, coating vehicle, or uncoated metal were performed in a similar fashion as described above, with the following modifications: 48-well plates were used to hold the disks during the assay period to facilitate manipulation of the disks and twice the volume of cell suspension was applied (200 µl/well). Exemplary amounts of total protein covalently attached to each disk were approximately 100 micrograms. Post-adhesion, the wells were washed twice in dPBS, using a swirling motion to dislodge non-specifically adhered cells. Wells were fixed for 10 minutes at 25° C. in 4% neutral buffered formalin, washed three times in dPBS, permeabilized in 0.5% Triton X-100 (dPBS), blocked in 5% nonfat milk (dPBS), and stained for actin fiber assembly with Oregon Green 488-conjugated phalloidin (Molecular Probes/Invitrogen, Carlsbad, Calif.). The disks were mounted to modified microscope slides with Vectashield mounting medium+DAPI (Vector Laboratories, Burlingame, Calif.) and imaged under a mercury lamp on a Zeiss Axioplan 2 microscope equipped with a Zeiss Axiocam digital camera.

Migration Assays

Briefly, 16 h before the assay, 70% confluent 75 cm² flasks of human melanoma A2058 cell (ATCC, passage 3-12) or human aortic endothelial cells (HAEC; Cambrex, passage 4-7) were kept in basal media (dMEM+0.1% BSA, or EBM-2+1% FCS, respectively). Cells were lifted with 0.25% Trypsin/1 mM EDTA, diluted in 0.5% BSA (dMEM) and washed 3 times in basal media (dMEM+0.1% BSA) or (EBM-2+0.1% FCS,) and recovered in suspension at working density ($2\times10^6$/ml for A2058 or $1.5\times10^6$ HAEC) for 1 h at 37° C. (5% $CO_2$). For migration-inhibition assays, the cells were preincubated during the recovery period for 30 minutes in 25 µg/ml anti-integrin antibodies (Chemicon, Temecula, Calif.) or control IgG (Jackson ImmunoResearch, Inc.). All migration assays were performed in triplicate in a 48-well Boyden chamber apparatus (NeuroProbe, Cabin John, Md.). The recovered cells were added to the bottom chambers in a volume of 30 µl. The wells were overlayed with an 8 µm-pore polycarbonate membrane (NeuroProbe, Cabin John, Md.) and coated with 100 µg/ml Rat tail collagen (Trevigen, Gaithersburg, Md.) for A2058 cells or acetylated 1% gelatin from porcine skin (Sigma, St. Louis, Mo.) for HAEC. The apparatus was assembled and stored inverted at 37° C. (5 $CO_2$) for a 2 h adhesion-period. The apparatus was re-inverted and 52 µl of the chemoattractants, 10 mg/ml Fibronectin, 200 ng/ml Tropoelastin, 10 µM elastin-derived peptides; VGVAPG (SEQ ID No. 5), and IFPGGACLGKACGRKRK (SEQ ID No. 6 (Cterm peptide) or 0.1% BSA/dMEM (diluent, random migration control), were added to the upper chambers and the migration was allowed to proceed for 2 h in a humidified incubator at 37° C. (5% $CO_2$). The membranes were then removed, fixed in methanol, stained with a Hema 3 stain set (Fisher Scientific, Pittsburgh, Pa.) and mounted migrated-side down to a 50×75 mm glass slide. Before 90% mounting medium (in xylenes) was applied, the non-migrated cells were removed from the exposed, non-migrated face of the membrane with a moistened swab. Readings represent the number of cells migrating through the membrane (the sum of two high power X 20 fields/well, averaged for each sextuplicate-well set).

CD34+ Cell Purification

Human CD34+ cells were purified from a peripheral blood mononuclear cell preparation collected by an apheresis procedure. The donor was mobilized with 10 µg/kg granulocyte colony-stimulating factor (G-CSF) for four days prior to the collection procedure, as approved by the Institutional Review Board of the University of Utah. Purification of CD34+ cells was accomplished in a closed and sterile system using an automated cell selection device, Clini-MACS (Miltenyi Biotec, Auburn, Calif.). Target cells were labeled with super-paramagnetic particles comprised of iron oxide and dextran conjugated to murine CD34 monoclonal antibodies. After labeling, the cells were separated using a high-gradient magnetic separation column. The magnetically labeled cells were retained in the magnetized column while the unlabeled cells passed through. The CD34+ cells were recovered by removing the magnetic field from the column and washing the cells out into a collection bag.

Analysis of CD34+ enrichment and purity was accomplished by flow cytometry using a FACScan analyzer (Becton Dickinson, San Jose, Calif.). Cells were stained with the monoclonal antibodies CD45-FITC and CD34-PE (Becton Dickinson, San Jose, Calif.) in addition to the viability probe 7-amino actinomycin-D (Sigma-Aldrich, St, Louis, Mo.). Briefly, data analysis was performed by gating on all leukocytes (CD45 positive cells) and all viable (7-AAD negative) cells to examine the CD34-PE expression compared to an isotype ($IgG_{2a}$-PE) control. At least 100,000 viable leukocytes were analyzed to determine the percentage of CD34 positive cells. Cells used for the experiment were 98% CD34+ cells.

Recombinant Human Tropoelastin

The endogenous signal sequence was removed and replaced with a 10×-histidine tag. This cDNA was cloned into an Isopropyl-β-D-Thiogalactoside (IPTG)-inducible construct (pET System, Novagen/EMD Biosciences, San Diego, Calif.) and expressed in the E. coli host strain Rosetta-2 (DE3) pLysS (Novagen). LB growth media containing 50 µg/ml ampicillin and 34 µg/ml chloramphenicol were inoculated with Rosetta-2 (DE3) pLysS bacteria containing the recombinant tropoelastin plasmid, and the culture was grown at 37° C. until optical density at 600 nm was 0.4-0.6. Induction was accomplished by adding IPTG to a final concentration of 1 mM, and the culture was incubated at 37° C. for 4 h. The bacterial pellet was harvested by centrifugation at 16,000×g for 20 min at 4° C. The pellet was resuspended in Bugbuster HT+lysozyme, and inclusion bodies were purified by washing (a total of 4×) with Bugbuster diluted 1:10 with deionized H2O followed by centrifugation at 4o at 5,000×g. Following the last wash, the inclusion bodies were harvested by centrifugation at 16,000×g for 1.5 min at 4° C. Inclusion bodies were resuspended in 1× Bind Buffer (500 mM NaCl, 20 mM Tris-HCl, 5 mM imidazole) containing 6 M urea that had been adjusted to pH 7.9 (following addition of the urea). Pellet was allowed to dissolve at 4° C. overnight. Insoluble material was then removed by centrifugation at 16,000×g for 30 minutes. The supernatant was tittered through a 0.45 µm syringe filter. The sample was then added to His-Mag beads (Novagen) that had been pre-equilibrated to 1× Bind Buffer with 6M urea and placed on a rocker for 5 minutes. Beads were collected using a Magnatight stand (Novagen) and washed×4 with 1× Wash Buffer (500 mM NaCl, 60 mM imidazole, 20 mM Tris-HCl) containing 6M urea (adjusted to pH 7.9). After the final wash, protein was eluted from the beads with 500 mM imidazole, 500 mM NaCl, 20 mM Tris-HCl, 6M urea, pH 7.9. The sample was then dialyzed against HBSS using Slide-A-Lyzer Dialysis Cassettes with 10,000 MWCO (Pierce). Obtained protein was analyzed by SDS-PAGE analysis by standard techniques and stored at −80° C.

Other Reagents

Human collagen I and fibronectin for adhesion experiments, were purchased from Biomedical Technologies Inc. (Stoughton, Mass.). Elastin-derived peptides were synthesized at the DNA Peptide Facility, University of Utah.

REFERENCES

WO00/50068
Olson et al. (1995) *Hum Mol Genet.* 4(9): 1677-9.
Curran et al. (1993) *Cell* 73: 159-168.
Ewart et al. (1993) *Nat Genet* 5: 11-16.
Li et al. (1997) *Hum. Mol. Genet.* 6: 1021-1028.
Dietz and Mecham (2000) *Matrix Biol.* 19: 481-486.
Li et al. (1998) *Nature* 393: 276-280.
Li et al. (1998) *J. Clin. Invest.* 102: 1783-1787.
Karnik et al. (2003) *Matrix Biology* 22: 409-425
Karnik et al. (2003) *Development* 130: 411-423
Brooke et al. (2003) *Trend in Cardiovascular Medicine* 13: 176-181

All publications, patents and patent applications are herein incorporated by reference in their entirety to the same extent as if each individual publication, patent or patent application was specifically and individually indicated to be incorporated by reference in its entirety.

Equivalents

Those skilled in the art will recognize, or be able to ascertain using no more than routine experimentation, many equivalents to the specific embodiments of the invention described herein. Such equivalents are intended to be encompassed by the following claims.

The invention claimed is:

1. An implantable medical device coated with a fragment of human tropoelastin, wherein said fragment consists of 17 consecutive amino acids and has at least 80% amino acid sequence identity to the amino acid sequence of SEQ ID NO: 6.

2. The device of claim 1, wherein the human tropoelastin fragment is covalently attached to the device.

3. The device of claim 1, wherein the human tropoelastin fragment is in an amount effective to promote adhesion of endothelial cells to the device.

4. The device of claim 3, wherein the endothelial cells are endothelial stem cells or endothelial progenitor cells.

5. The device of claim 3, wherein the amount of the human tropoelastin fragment is at least 100 ng per square centimeter.

6. The device of claim 1, comprising a metal, an alloy or a plastic.

7. The device of claim 6, wherein the metal comprises stainless steel.

8. The device of claim 1, further comprising a biocompatible polymer.

9. The device of claim 8, wherein the biocompatible polymer is selected from the group consisting of dacron, polyurethane, polypropylene, or polytetrafluoroethylene (PTFE).

10. The device of claim 1, further comprising an anti-CD34 antibody.

11. The device of claim 10, wherein the anti-CD34 antibody is monoclonal.

12. The device of claim 1, wherein the device is a catheter, stent, shunt, wire, or other intraluminal device.

13. The device of claim 1, wherein the device is a pacemaker, cardioverter-defibrillator, artificial valve, or vascular graft.

14. The device of claim 1, comprising metal, plastic, silicone, dacron, polyurethane, polypropylene, PTFE, or derivatives thereof.

* * * * *